(12) United States Patent
Whitlow et al.

(10) Patent No.: US 6,824,782 B2
(45) Date of Patent: Nov. 30, 2004

(54) POLYALKYLENE OXIDE-MODIFIED SINGLE CHAIN POLYPEPTIDES

(75) Inventors: Marc Whitlow, El Sobrante, CA (US); Robert G. L. Shorr, Edison, NJ (US); David R. Filpula, Piscataway, NJ (US); Lihsyng Stanford Lee, Princeton Junction, NJ (US)

(73) Assignee: Enzon, Inc., Piscataway, NJ (US)

( * ) Notice: Subject to any disclaimer, the term of this patent is extended or adjusted under 35 U.S.C. 154(b) by 399 days.

(21) Appl. No.: 09/791,540

(22) Filed: Feb. 26, 2001

(65) Prior Publication Data

US 2002/0098192 A1 Jul. 25, 2002

Related U.S. Application Data

(63) Continuation of application No. 09/069,842, filed on Apr. 30, 1998, now abandoned.
(60) Provisional application No. 60/044,449, filed on Apr. 30, 1997, provisional application No. 60/050,472, filed on Jun. 23, 1997, provisional application No. 60/063,074, filed on Oct. 27, 1997, and provisional application No. 60/067,341, filed on Dec. 2, 1997.

(51) Int. Cl.[7] .................... A61K 39/395; C07K 16/46
(52) U.S. Cl. .................. 424/178.1; 530/389.1; 530/391.1
(58) Field of Search ............... 424/178.1; 530/389.1, 530/391.1

(56) References Cited

U.S. PATENT DOCUMENTS

| | | | |
|---|---|---|---|
| 4,179,337 A | 12/1979 | Davis et al. | 435/181 |
| 4,704,692 A | 11/1987 | Ladner | 364/496 |
| 4,881,175 A | 11/1989 | Ladner | 364/496 |
| 4,904,582 A | 2/1990 | Tullis | 435/6 |
| 4,946,778 A | 8/1990 | Ladner et al. | 435/69.6 |
| 5,049,504 A | 9/1991 | Maugh et al. | 435/252.33 |
| 5,091,513 A | 2/1992 | Huston et al. | 530/387 |
| 5,122,614 A | 6/1992 | Zalipsky | 548/520 |
| 5,166,320 A | 11/1992 | Wu et al. | 530/395 |
| 5,202,236 A | 4/1993 | Maugh et al. | 435/69.1 |
| 5,202,256 A | 4/1993 | Maugh et al. | 435/252.3 |
| 5,212,075 A | 5/1993 | Bednarski et al. | 435/72 |
| 5,258,498 A | 11/1993 | Huston et al. | 530/350 |
| 5,260,203 A | 11/1993 | Ladner et al. | 435/172.1 |
| 5,438,040 A | 8/1995 | Ekwuribe | 514/3 |
| 5,443,953 A | 8/1995 | Hansen et al. | 424/1.49 |
| 5,455,030 A | 10/1995 | Ladner et al. | 424/435.1 |
| 5,482,858 A | 1/1996 | Huston et al. | 435/252.33 |
| 5,518,889 A | 5/1996 | Ladner et al. | 435/7.93 |
| 5,521,291 A | 5/1996 | Curiel et al. | 530/391.7 |
| 5,534,254 A | 7/1996 | Huston et al. | 424/135.1 |
| 5,547,932 A | 8/1996 | Curiel et al. | 435/65 |
| 5,635,603 A | 6/1997 | Hansen et al. | 530/391.5 |
| 5,656,465 A | 8/1997 | Panicali et al. | 435/172.3 |
| 5,661,025 A | 8/1997 | Szoka, Jr. et al. | 435/172.3 |
| 5,714,350 A | 2/1998 | Co et al. | 435/69.6 |
| 5,753,204 A | 5/1998 | Huston et al. | 424/1.49 |
| 5,844,107 A | 12/1998 | Hanson et al. | 536/23.1 |
| 5,853,723 A | 12/1998 | Jacobs et al. | 424/178.1 |
| 5,869,620 A | 2/1999 | Whitlow et al. | 530/387.3 |
| 5,872,222 A | 2/1999 | Chang | 530/391.1 |
| 5,888,773 A | 3/1999 | Jost et al. | 435/69.6 |
| 5,981,273 A | 11/1999 | Curiel et al. | 435/320.1 |
| 5,990,275 A | 11/1999 | Whitlow et al. | 530/324 |
| 5,998,144 A | 12/1999 | Reff et al. | 435/6 |
| 6,022,735 A | 2/2000 | Curiel et al. | 435/320.1 |
| 6,025,158 A | 2/2000 | Gonzalez et al. | 435/69.1 |
| 6,027,725 A | 2/2000 | Whitlow et al. | 424/136.1 |
| 6,077,663 A | 6/2000 | Curiel et al. | 435/6 |
| 6,117,980 A | 9/2000 | Gonzalez et al. | |
| 6,333,396 B1 * | 12/2001 | Filpula et al. | 530/387.3 |

FOREIGN PATENT DOCUMENTS

| | | |
|---|---|---|
| WO | 9119739 | * 12/1991 |
| WO | WO 92/16555 | 10/1992 |
| WO | WO 93/11161 | 6/1993 |
| WO | WO 94/04691 | 3/1994 |
| WO | WO 94/12520 | 6/1994 |
| WO | WO 95/11020 | 4/1995 |
| WO | 9609325 | * 3/1996 |
| WO | WO 96/09325 | 3/1996 |
| WO | WO 96/13599 | 5/1996 |
| WO | WO 96/23794 | 8/1996 |
| WO | WO 96/40731 | 12/1996 |
| WO | WO 97/14719 | 4/1997 |
| WO | WO 98/25971 | 6/1998 |
| WO | WO 99/64460 | 12/1999 |

OTHER PUBLICATIONS

Abuchowski, A. et al., "Alteration of Immunological Properties of Bovine Serum Albumin by Covalent Attachment of Polyethylene Glycol," *J. Biol. Chem.* 252:3578–3581, The American Society of Biological Chemists, Inc. (1977).

(List continued on next page.)

*Primary Examiner*—Bennett Celsa
(74) *Attorney, Agent, or Firm*—Muserlian, Lucas and Mercanti

(57) ABSTRACT

The present invention relates to the chemical modification of single chain polypeptides by means of covalent attachment of strands of poly(ethylene glycol) PEG and similar poly (alkylene oxides) to single chain polypeptide binding molecules that have the three dimensional folding and, thus, the binding ability and specificity, of the variable region of an antibody. Such preparations of modified single chain polypeptide binding molecules have reduced immugenicity and antigenicity as well as having a longer halflife in the bloodstream as compared to the parent polypeptide. These beneficial properties of the modified single chain polypeptide binding molecules make them very useful in a variety of therapeutic applications. The invention also relates to multivalent antigen-binding molecules capable of PEGylation. Compositions of, genetic constructs for, methods of use, and methods for producing PEGylated antigen-binding proteins are disclosed.

13 Claims, 10 Drawing Sheets

OTHER PUBLICATIONS

Abuchowski, A. and F.F. Davis, "Soluble Polymer–Enzyme Adducts," in: Enzymes as Drugs, Holcenberg, J.S. and J. Roberts, eds., John Wiley & Sons, Inc., New York, NY, pp. 367–383 (1981).

Abuchowski, A. et al., "Cancer Therapy with Chemically Modified Enzymes. I. Antitumor Properties of Polyethylene Glycol–Asparaginase Conjugates," *Cancer Biochem. Biophys.* 7:175–186, Gordon and Breach Science Publishers, Inc. (1984).

Amit, A.G et al., "Three Dimensional Structure of an Antigen–Antibody Complex at 2.8 Å Resolution," *Science* 233:747–753, Association for the Advancement of Science (1986).

Anand, N.N. et al., "Bacterial Expression and Secretion of Various Single–chain Fv Genes Encoding Proteins Specific for a *Salmonella* Serotype B O–Antigen," *J. Biol. Chem.* 266:21874–21879, The American Society for Biochemistry and Molecular Biology, Inc. (1991).

Avrameas, A. et al., "Polyreactive anti–DNA monoclonal antibodies and a derived peptide as vectors for the intracytoplasmic and intranuclear translocation of macromolecules," *Proc. Natl. Acad. Sci. USA* 95:5601–5606, The National Academy of Sciences of the USA (May 1998).

Beauchamp, C.O. et al., "A New Procedure for the Synthesis of Polyethylene Glycol–Protein Adducts; Effects on Function, Receptor Recognition, and Clearance of Superoxide Dismutase, Lactoferrin, and $\alpha_2$–Macroglobulin," *Analytical Biochem.* 131:25–33, Academic Press, Inc. (1983).

Benhar, I. et al., "Mutations of Two Lysine Residues in the CDR Loops of a Recombinant Immunotoxin That Reduce Its Sensitivity to Chemical Derivatization," *Bioconj. Chem.* 5:321–326, American Chemical Society (1994).

Bird, R.E. et al., "Single–Chain Antigen–Binding Proteins," *Science* 242:423–426, Association for the Advancement of Science (1988).

Bogdanov Jr., A., et al., "Graft Copolymers as Carriers for Systemic Delivery of Expression Vectors," *Proceed. Intl. Symp. Control. Rel. Bioact. Mater.* 25:91–92, The Controlled Release Society, Inc. (Jun. 1998).

Chen, S.–Y. et al., "Design of a genetic immunotoxin to eliminate toxin immunogenicity," *Gene Ther.* 2:116–123, Stockton Press (1995).

Co, M.S. et al., "Chimeric and Humanized Antibodies with Specificity for the CD33 Antigen," *J. Immunol.* 148:1149–1154, The American Association of Immunologists (1992).

Colcher, D. et al., "In Vivo Tumor Targeting of a Recombinant Single–Chain Antigen–Binding Protein," *J. Natl. Cancer Inst.* 82:1191–1197, The National Cancer Institute (1990).

Cumber, A.J. et al., "Comparative Stabilities In Vitro and In Vivo of a Recombinant Mouse Antibody FvCys Fragment and A bisFvCys Conjugate," *J. Immunol.* 149:120–126, The American Association of Immunologists (1992).

Delente, J.J., "Glycosylation revisited," *Trends in Biotechnol.* 3:218, Elsevier Science Publishers B.V. (1985).

Desplancq, D. et al., "Multimerization behaviour of single chain Fv variants for the tumour–binding antibody B72.3," *Protein Engineering* 7:1027–1033, Oxford University Press (1994).

Eldin, P. et al., "High–level secretion of two antibody single chain Fv fragments by *Pichia pastoris*," *J. Immunol. Meth.* 201:67–75, Elsevier Science B.V. (Feb. 1997).

Filpula, D. et al., "Production of single–chain Fv monomers and multimers," in *Antibody Engineering: A Practical Approach,* McCafferty, J., et al., eds., IRL Press (Oxford University Press), Oxford, UK, pp. 253–268 (Aug. 1996).

Filpula, D., "PEGylated sFv and Glycosylated sFv," Slide Presentation at: IBC's Eighth Annual International Conference on Antibody Engineering: New Technology, Application & Commercialization, Dec. 3, 1997.

Filpula, D., "PEGylated sFv and Glycosylated sFv," Abstract from: IBC's Eighth Annual International Conference on Antibody Engineering: New Technology, Application & Commercialization, meeting date Dec. 3, 1997.

Fominaya, J. and W. Wels, "Target Cell–specific DNA Transfer Mediated by a Chimeric Multidomain Protein," *J. Biol. Chem.* 271:10560–10568, The American Society for Biochemistry and Molecular Biology, Inc. (May 1996).

Gavel, Y., and G. von Heijne, "Sequence differences between glycosylated and non–glycosylated Asn–X–Thr/Ser acceptor sites: implications for protein engineering," *Protein Engineering* 3:433–442, Oxford University Press (1990).

George, A.J.T. et al., "Production of a Bispecific Antibody by Linkage of Two Recombinant Single Chain Fv Molecules," *J. Cell. Biochem. Suppl.* 15E:127, Abstract No. N 206, Wiley–Liss (1991).

Goodson, R.J. and N.V. Katre, "Site–Directed Pegylation of Recombinant Interleukin–2 at Its Glycosylation Site," *Bio/Technology* 8:343–346, Nature Publishing Co. (1990).

Greenman, J. et al., "The use of intracellular single–chain antibody fragments to inhibit specifically the expression of cell surface molecules," *J. Immunol. Meth.* 194:169–180, Elsevier Science B.V. (Aug. 1996).

Greenwald, R.B., "Drug delivery systems: anticancer prodrugs and their polymeric conjugates," *Exp. Opin. Ther. Patents* 7:601–609, Ashley Publications Ltd. (Jun. 1997).

Hämmerling, G.J. et al., "Appendix. Production of Antibody–Producing Hybridomas in the Rodent Systems," in *Monoclonal Antibodies and T–Cell Hybridomas,* Hämmerling, G.J. et al., eds., Elsevier/North–Holland Biomedical Press, Amsterdam, The Netherlands, pp. 563–587 (1981).

Hershfield, M.S. et al., "Use of site–directed mutagenesis to enhance the epitope–shielding effect of covalent modification of proteins with polyethylene glycol," *Proc. Natl. Acad. Sci. USA* 88:7185–7189, The National Academy of Science of the USA (1991).

Holliger, P. et al., "'Diabodies': Small bivalent and bispecific antibody fragments," *Proc. Natl. Acad. Sci. USA* 90:6444–6448, The National Academy of Sciences of the USA (1993).

Hooftman, G. et al., "Review Poly(ethylene glycol)s with Reactive Endgroups. II. Practical Consideration for the Preparation of Protein–PEG Conjugates," *J. Bioactive Compat. Polymers* 11:135–159, Technomic Publishing Co., Inc. (Apr. 1996).

Hoogenboom, H.R., "Mix and match: Building manifold binding sites," *Nature Biotech.* 15:125–126, Nature Publishing Co. (Feb. 1997).

Huber, R., "Structural Basis for Antigen–Antibody Recognition," *Science* 233:702–703, American Association for the Advancement of Science (1986).

Inada, Y. et al., "Biomedical and biotechnological applications of PEG– and PM–modified proteins," *Trends Biotech.* 13:86–91, Elsevier Science Ltd (1995).

Jost, C.R., et al., "Mammalian Expression and Secretion of Functional Single–chain Fv Molecules," *J. Biol. Chem.* 269:26267–26273, American Society for Biochemistry and Molecular Biology, Inc. (1994).

Keck, P.C., and J.S. Huston, "Symmetry of Fv Architecture Is Conducive to Grafting a Second Antibody Binding Site in the Fv Region," *Biophys. J.* 71:2002–2011, Biophysical Society (Oct. 1996).

Kimura, M. et al., "A New Tactic for the Treatment of Jaundice: An Injectable Polymer–Conjugated Bilirubin Oxidase (42747)," *Proc. Soc. Exper. Biol. & Med.* 188:364–369, The Society for Experimental Biology and Medicine (1988).

Köhler, G. and C. Milstein, "Continuous cultures of fused cells secreting antibody of predefined specificity," *Nature* 256:495–497, Macmillan Magazines Ltd. (1975).

Köhler, G. and C. Milstein, "Derivation of specific antibody–producing tissue culture and tumor lines by cell fusion," *Eur. J. Immunol.* 6:511–519, Wiley–VCH (1976).

Köhler, G. et al., "Fusion between immunoglobulin–secreting and nonsecreting myeloma cell lines," *Eur. J. Immunol.* 6:292–295, Wiley–VCH (1976).

Ladd, D. and R. Snow, "Reagents for the Preparation of Chromophorically Labeled Polyethylene Glycol–Protein Conjugates," *Anal. Biochem.* 210:258–261, Academic Press, Inc. (1993).

Leung, S.–o. et al., "Effect of VK Framework–1 Glycosylation on the Binding Affinity of Lymphoma–Specific Murine and Chimeric LL2 Antibodies and Its Potential Use as a Novel Conjugation Site," *Int. J. Cancer* 60:534–538, Wiley–Liss, Inc. (1995).

Leung, S.–o. et al., "Engineering a Unique Glycosylation Site for Site–Specific Conjugation of Haptens to Antibody Fragments," *J. Immunol.* 154:5919–5926, The American Association of Immunologists (1995).

Luo, D., et al., "An Engineered Bivalent Single–Chain Antibody Fragment That Increases Antigen Binding Activity," *J. Biochem* 121:831–834, The Japanese Biochemical Society (May 1997).

Marasco, W.A. et al., "Simple Single–Chain Antibody Fusion Proteins as DNA Carriers," in: *IBC's Eighth Annual International Conference on Antibody Engineering: New Technology, Application & Commercialization,* Dec. 3–5, 1997, Hotel del Coronado, Coronado, CA, International Business Communications, 1 p. (Dec. 1997).

Milenic, D.E. et al., "Construction, Binding Properties, Metabolism, and Tumor Targeting of a Single–Chain $F_v$ Derived from the Pancarcinoma Monoclonal Antibody CC49," *Cancer Res.* 51:6363–6371, The American Association for Cancer Research (1991).

Monfardini, C. et al., "A Branched Monomethoxypoly(ethylene glycol) for Protein Modification," *Bioconj. Chem.* 6:62–69, American Chemical Society (1995).

Muyldermans, S. et al., "Sequence and structure of $V_H$ domain from naturally occurring camel heavy chain immunoglobulins lacking light chains," *Protein Engin.* 7:1129–1135, Oxford University Press (1994).

Nathan, A. et al., "Copolymers of Lysine and Polyethylene Glycol: A New Family of Functionalized Drug Carriers," *Bioconj. Chem.* 4:54–62, American Chemical Society (1993).

Nishimura, H. et al., "Improved Modification of Yeast Uricase with Polyethylene Glycol, Accompanied with Non-immunoreactivity towards Anti–Uricase Serum and High Enzymic Activity," *Enzyme* 26:49–53, S. Karger (1981).

Pai, L.H. et al., "Anti–tumor activities of immunotoxins made of monoclonal antibody B3 and various forms of *Pseudomonas* exotoxin," *Proc. Natl. Acad. Sci. USA* 88:3358–3362. National Academy of Sciences of the USA (1991).

Panka, D.J. et al., "Variable region framework differences result in decreased or increased affinity of variant anti–digoxin antibodies," *Proc. Natl. Acad. Sci. USA* 85:3080–3084, National Academy of Sciences of the USA (1988).

Pardridge, W.M. et al., "Enhanced Endocytosis in Cultured Human Breast Carcinoma Cells and In Vivo Biodistribution in Rats of a Humanized Monoclonal Antibody after Cationization of the Protein," *J. Pharmacol. & Exper. Therapeut.* 286:548–554, The American Society for Pharmacology and Experimental Therapeutics (Jul. 1998).

Plank, C. et al., "Branched Cationic Peptides for Gene Delivery: Role of Type and Number of Cationic Residues in Formation and in Vitro Activity of DNA Polyplexes," *Human Gene Ther.* 10:319–332, Mary Ann Liebert (Jan. 1999).

Prammer, K.V. and L. Otvos, Jr., "Structural Effects of Glycosylation on the C–Terminal Pentapeptide of Peptide T," *Biomedical Peptides. Proteins & Nucl. Acids* 1:221–226, Mayflower Worldwide Ltd. (1995).

Reiter, Y., et al., "Engineering antibody Fv fragments for cancer detection and therapy: Disulfide–stabilized Fv fragments," *Nature Biotechnology* 14:1239–1245, Nature Publishing Co. (Oct. 1996).

Ridder, R. et al., "Generation of Rabbit Monoclonal Antibody Fragments from a Combinatorial Phage Display Library and Their Production in the Yeast *Pichia pastoris*," *Bio/Technology* 13:255–260, Nature Publishing Co. (1995).

Robinson, P. et al., "Effect of Polyethylene Glycol Conjugated to DNA–Transfecting Complexes Targeted at the Transferrin Receptor of HeLa Cells," *Drug Delivery* 4:115–119, Taylor & Francis (Apr. 1997).

Rudikoff, S. et al., "Single amino acid substitution altering antigen–binding specificity," *Proc. Natl. Acad. Sci. USA* 79:1979–1983, National Academy of Sciences of the USA (1982).

Schaffhausen, B.S., "Chapter 21. Designing and Using Site–Specific Antibodies to Synthetic Peptides," in: *Hybridoma Technology in the Biosciences and Medicine,* Springer, T.A., ed., Plenum Press, NY, pp. 355–373 (1985).

Sela, M. and E. Hurwitz, "Chapter 10. Conjugates of Antibodies with Cytotoxic Drugs," in: *Immunoconjugates. Antibody Conjugates in Radioimaging and Therapy of Cancer,* Vogel, C.–W., ed., Oxford University Press, New York, NY, pp. 189–195 (1987).

Sharp, K.A. et al., "Synthesis and Application of a Poly(ethylene glycol)–Antibody Affinity Ligand for Cell Separations in Aqueous Polymer Two–Phase Systems," *Analytical Biochem.* 154:110–117, Academic Press, Inc. (1986).

Skerra, A., et al., "The Functional Expression of Antibody $F_v$ Fragments in *Escherichia coli:* Improved Vectors and a Generally Applicable Purification Technique," *Bio/Technology* 9:273–278, Nature Publishing Co. (1991).

Suzuki, T. et al., "Physicochemical and Biological Properties of Poly(Ethylene Glycol)–Coupled Immunoglobulin G," *Biochim. et Biophys. Acta* 788:248–255, Elsevier Science Publishers B.V. (1984).

Verhaar, M.J. et al., "Technetium–99m Radiolabeling Using a Phage–Derived Single–Chain Fv with a C–Terminal Cysteine," *J. Nucl. Med.* 37:868–872, Society of Nucler Medicine, Inc. (May 1996).

Veronese, F.M. et al., "Surface Modification of Proteins: Activation of Monomethoxy–Polyethylene Glycols by Phenylchloroformates and Modification of Ribonuclease and Superoxide Dismutase," *Appl. Biochem. Biotechnol.* 11:141–152, The Humana Press, Inc. (1985).

Wadhwa, M.S., et al., "Peptide–Mediated Gene Delivery: Influence of Peptide Structure on Gene Expression," *Bioconjugate Chem.* 8:81–88, American Chemical Society (Jan. 1997).

Wang, M. et al., "Single–chain Fv with manifold N–glycans as bifunctional scaffolds for immunomolecules," *Prot. Eng.* 11:1277–1283, Oxford University Press (Dec. 1998).

Wang, Q.-c. et al., "Polyethylene Glycol–modified Chimeric Toxin Composed of Transforming Growth Factor α and *Pseudomonas* Exotoxin," *Cancer Res.* 53:4588–4594, American Association for Cancer Research (1993).

Whitlow, M. et al., "1.85 Å structure of anti–fluorescein 4–4–20 Fab," *Protein Engineering* 8:749–761, Oxford Unviersity Press (1995).

Whitlow, M., et al., "An improved linker for single–chain Fv with reduced aggregation and enhanced proteolytic stability," *Protein Engin.* 6:989–995, Oxford University Press (1993).

Whitlow, M. and D. Filpula, "Single–Chain Fv Proteins and Their Fusion Proteins," *Methods: A Companion to Methods in Enzymology* 2:97–105, Academic Press, Inc. (1991).

Whitlow, M. et al., "Multivalent Fvs: characterization of single–chain Fv oligomers and preparation of a bispecific Fv," *Protein Engin.* 7:1017–1026, Oxford University Press (1994).

Wright, A. et al., "Antibody variable region glycosylation: position effects on antigen binding and carbohydrate structure," *EMBO J.* 10:2717–2723, Oxford University Press (1991).

Wright, A. and S.L. Morrison, "Antibody variable region glycosylation: biochemical and clinical effects," *Springer Semin. Immunopathol.* 15:259–273, Springer–Verlag (1993).

Yokota, T. et al., "Rapid Tumor Penetration of a Single–Chain Fv and Comparison with Other Immunoglobulin Forms," *Cancer Res.* 52:3402–3408, The American Association for Cancer Research (1992).

Zalipsky, S., "Synthesis of an End–Group Functionalized Polyethylene Glycol–Lipid Conjugate for Preparation of Polymer–Grafted Liposomes," *Bioconj. Chem.* 4:296–299, American Chemical Society (1993).

Zalipsky, S., "Functionalized Poly(ethylene glycol) for Preparation of Biologically Relevant Conjugates," *Bioconj. Chem* 6:150–165, American Chemical Society (1995).

Zalipsky, S., "Chemistry of polyethylene glycol conjugates with biologically active molecules," *Adv. Drug Del. Reviews.* 16:157–182, Elsevier Science B.V. (1995).

Zalipsky, S. et al., "Peptide Attachment to Extremities of Liposomal Surface Grafted PEG Chains: Preparation of the Long–Circulating Form of Laminin Pentapeptide, YIGSR," *Bioconj. Chem.* 6:705–708, American Chemical Society (1995).

Zalipsky, S. et al., "Poly(ethylene glycol)–Grafted Liposomes with Oligopeptide or Oligosaccharide Ligands Appended to the Termini of the Polymer Chains," *Bioconj. Chem.* 8:111–118, American Chemical Society (Mar. 1997).

* cited by examiner

```
CC49 V_L                                        12              15
 D   V   V   M   S   Q   S   P   S   S   L   P   V   S   V
GAC GTC GTG ATG TCA CAG TCT CCA TCC TCC CTA CCT GTG TCA GTT
Aat II
                                                        27C
 G   E   K   V   T   L   S   C   K   S   S   Q   S   L   L
GGC GAG AAG GTT ACT TTG AGC TGC AAG TCC AGT CAG AGC CTT TTA
                                                        39
 Y   S   G   N   Q   K   N   Y   L   A   W   Y   Q   Q   K
TAT AGT GGT AAT CAA AAG AAC TAC TTG GCC TGG TAC CAG CAG AAA
                                                        54
 P   G   Q   S   P   K   L   L   I   Y   W   A   S   A   R
CCA GGG CAG TCT CCT AAA CTG CTG ATT TAC TGG GCA TCC GCT AGG
                                                        69
 E   S   G   V   P   D   R   F   T   G   S   G   S   G   T
GAA TCT GGG GTC CCT GAT CGC TTC ACA GGC AGT GGA TCT GGG ACA
                                77                      84
 D   F   T   L   S   I   S   C   V   K   T   E   D   L   A
GAT TTC ACT CTC TCC ATC AGC TGT GTG AAG ACT GAA GAC CTG GCA
                                *
                                                        99
 V   Y   Y   C   Q   Q   Y   Y   S   Y   P   L   T   F   G
GTT TAT TAC TGT CAG CAG TAT TAT AGC TAT CCC CTC ACG TTC GGT
                     218 Linker
 A   G   T   K   L   V   L   K   G   S   C   S   G   S   G
GCT GGG ACC AAG CTT GTG CTG AAA GGC TCT TGT TCC GGT AGC GGC
             Hind III                   *
                                    CC49 V_H            4
 K   P   G   S   G   E   G   S   T   K   G   Q   V   Q   L
AAA CCC GGG AGT GGT GAA GGT AGC ACT AAA GGT CAG GTT CAG CTG
     Sma I                                      PvuII
                                13                      19
 Q   Q   S   D   A   E   L   V   K   P   G   A   S   V   K
CAG CAG TCT GAC GCT GAG TTG GTG AAA CCT GGG GCT TCA GTG AAG
                                                        34
 I   S   C   K   A   S   G   Y   T   F   T   D   H   A   I
ATT TCC TGC AAG GCT TCT GGC TAC ACC TTC ACT GAC CAT GCA ATT
                                                        49
 H   W   V   K   Q   N   P   E   Q   G   L   E   W   I   G
CAC TGG GTG AAA CAG AAC CCT GAA CAG GGC CTG GAA TGG ATT GGA
```

FIG.2A

```
                                              63
Y   F   S   P   G   N   D   D   F   K   Y   N   E   R   F
TAT TTT TCT CCC GGA AAT GAT GAT TTT AAA TAC AAT GAG AGG TTC
                                                          78
K   G   K   A   T   L   T   A   D   K   S   S   S   T   A
AAG GGC AAG GCC ACA CTG ACT GCA GAC AAA TCC TCC AGC ACT GCC
                    82B                                   90
Y   V   Q   L   N   C   L   T   S   E   D   S   A   V   Y
TAC GTG CAG CTC AAC TGC CTG ACA TCT GAG GAT TCT GCA GTG TAT
                    *
                                                         107
F   C   T   R   S   L   N   M   A   Y   W   G   Q   G   T
TTC TGT ACA AGA TCC CTG AAT ATG GCC TAC TGG GGT CAA GGA ACC
                112
S   V   T   V   S   C
TCA GTC ACC GTC TCC TGC TAA TAGGATCC
                    *       BamHI
```

FIG.2B

```
CC49 V_L                              12          15
 D   V   V   M   S   Q   S   P   S   S   L   P   V   S   V
GAC GTC GTG ATG TCA CAG TCT CCA TCC TCC CTA CCT GTG TCA GTT
Aat II
                                                        27C
 G   E   K   V   T   L   S   C   K   S   S   Q   S   L   L
GGC GAG AAG GTT ACT TTG AGC TGC AAG TCC AGT CAG AGC CTT TTA
                                                        39
 Y   S   G   N   Q   K   N   Y   L   A   W   Y   Q   Q   K
TAT AGT GGT AAT CAA AAG AAC TAC TTG GCC TGG TAC CAG CAG AAA
                                                        54
 P   G   Q   S   P   K   L   L   I   Y   W   A   S   A   R
CCA GGG CAG TCT CCT AAA CTG CTG ATT TAC TGG GCA TCC GCT AGG
                                                        69
 E   S   G   V   P   D   R   F   T   G   S   G   S   G   T
GAA TCT GGG GTC CCT GAT CGC TTC ACA GGC AGT GGA TCT GGG ACA
                    77                                  84
 D   F   T   L   S   I   S   S   V   K   T   E   D   L   A
GAT TTC ACT CTC TCC ATC AGC AGT GTG AAG ACT GAA GAC CTG GCA
                                                        99
 V   Y   Y   C   Q   Q   Y   Y   S   Y   P   L   T   F   G
GTT TAT TAC TGT CAG CAG TAT TAT AGC TAT CCC CTC ACG TTC GGT
                            218 Linker
 A   G   T   K   L   V   L   K   G   S   T   S   G   S   G
GCT GGG ACC AAG CTT GTG CTG AAA GGC TCT ACT TCC GGT AGC GGC
                 Hind III
                                          CC49 V_H      4
 K   P   G   S   G   E   G   S   T   K   G   Q   V   Q   L
AAA CCC GGG AGT GGT GAA GGT AGC ACT AAA GGT CAG GTT CAG CTG
     Sma I                                         Pvu II
                                13                      19
 Q   Q   S   D   A   E   L   V   K   P   G   A   S   V   K
CAG CAG TCT GAC GCT GAG TTG GTG AAA CCT GGG GCT TCA GTG AAG
                                                        34
 I   S   C   K   A   S   G   Y   T   F   T   D   H   A   I
ATT TCC TGC AAG GCT TCT GGC TAC ACC TTC ACT GAC CAT GCA ATT
                                                        49
 H   W   V   K   Q   N   P   E   Q   G   L   E   W   I   G
CAC TGG GTG AAA CAG AAC CCT GAA CAG GGC CTG GAA TGG ATT GGA
                                                        63
 Y   F   S   P   G   N   D   D   F   K   Y   N   E   R   F
TAT TTT TCT CCC GGA AAT GAT GAT TTT AAA TAC AAT GAG AGG TTC
```

FIG.3A

```
                                                              78
K   G   K   A   T   L   T   A   D   K   S   S   S   T   A
AAG GGC AAG GCC ACA CTG ACT GCA GAC AAA TCC TCC AGC ACT GCC
                    82B                                    90
Y   V   Q   L   N   S   L   T   S   E   D   S   A   V   Y
TAC GTG CAG CTC AAC AGC CTG ACA TCT GAG GAT TCT GCA GTG TAT
                                                          107
F   C   T   R   S   L   N   M   A   Y   W   G   Q   G   T
TTC TGT ACA AGA TCC CTG AAT ATG GCC TAC TGG GGT CAA GGA ACC
                112
S   V   T   V   S   K   K   K   K   K   K   K   K   V   T
TCG GTC ACC GTC TCC AAA AAG AAG AAA AAA AAG AAA AAG GTC ACC
 BstEII          *   *   *   *   *   *   *   *     BstEII

V   S
GTC TCC TAA TAGGATCC
             BamHI
```

FIG.3B 1 2 3 4 5 6 7 8 10

POLYALKYLENE OXIDE-MODIFIED SINGLE CHAIN POLYPEPTIDES

This application is a continuation of U.S. application No. 09/069,842 filed Apr. 30, 1998 now abandoned, which claims the benefit of the filing date of each of the following applications: U.S. Provisional Application No. 60/044,449 filed Apr. 30, 1997; U.S. Provisional Application No. 60/050,472 filed Jun. 23, 1997; U.S. Provisional Application No. 60/063,074 filed Oct. 27, 1997; and U.S. Provisional Application No. 60/067,341 filed Dec. 2, 1997, each of which is incorporated herein by reference in its entirety.

BACKGROUND OF THE INVENTION

1. Field of the Invention

The present invention relates to the chemical modification of single chain polypeptides by means of covalent attachment of strands of poly(ethylene glycol) PEG and similar poly(alkylene oxides) to single chain polypeptide binding molecules that have the three dimensional folding and, thus, the binding ability and specificity, of the variable region of an antibody. Such preparations of modified single chain polypeptide binding molecules have reduced immugenicity and antigenicity as well as having a longer halflife in the bloodstream as compared to the parent polypeptide. These beneficial properties of the modified single chain polypeptide binding molecules make them very useful in a variety of therapeutic applications. The invention also relates to multivalent antigen-binding molecules capable of PEGylation. Compositions of, genetic constructions for, methods of use, and methods for producing PEGylated antigen-binding proteins are disclosed.

2. Description of Related Art

Antibodies are proteins generated by the immune system to provide a specific molecule capable of complexing with an invading molecule, termed an antigen. Natural antibodies have two identical antigen-binding sites, both of which are specific to a particular antigen. The antibody molecule "recognizes" the antigen by complexing its antigen-binding sites with areas of the antigen termed epitopes. The epitopes fit into the conformational architecture of the antigen-binding sites of the antibody, enabling the antibody to bind to the antigen.

The antibody molecule is composed of two identical heavy and two identical light polypeptide chains, held together by interchain disulfide bonds. The remainder of this discussion on antibodies will refer only to one pair of light/heavy chains, as each light/heavy pair is identical. Each individual light and heavy chain folds into regions of approximately 110 amino acids, assuming a conserved three-dimensional conformation. The light chain comprises one variable region ($V_L$) and one constant region ($C_L$), while the heavy chain comprises one variable region ($V_H$) and three constant regions ($C_H1$, $C_H2$ and $C_H3$). Pairs of regions associate to form discrete structures. In particular, the light and heavy chain variable regions associate to form an "Fv" area which contains the antigen-binding site. The constant regions are not necessary for antigen binding and in some cases can be separated from the antibody molecule by proteolysis, yielding biologically active (i.e., binding) variable regions composed of half of a light chain and one quarter of a heavy chain.

Further, all antibodies of a certain class and their $F_{ab}$ fragments (i.e., fragments composed of $V_L$, $C_L$, $V_H$, and $C_H1$) whose structures have been determined by x-ray crystallography show similar variable region structures despite large differences in the sequence of hypervariable segments even when from different animal species. The immunoglobulin variable region seems to be tolerant towards mutations in the antigen-binding loops. Therefore, other than in the hypervariable regions, most of the so-called "variable" regions of antibodies, which are defined by both heavy and light chains, are, in fact, quite constant in their three dimensional arrangement. See for example, Huber, R., *Science* 233:702–703 (1986)).

Recent advances in immunobiology, recombinant DNA technology, and computer science have allowed the creation of single polypeptide chain molecules that bind antigen. These single-chain antigen-binding molecules ("SCA") or single-chain variable fragments of antibodies ("sFv") incorporate a linker polypeptide to bridge the individual variable regions, $V_L$ and $V_H$, into a single polypeptide chain. A description of the theory and production of single-chain antigen-binding proteins is found in Ladner et al., U.S. Pat. Nos. 4,946,778, 5,260,203, 5,455,030 and 5,518,889. The single-chain antigen-binding proteins produced under the process recited in the above U.S. patents have binding specificity and affinity substantially similar to that of the corresponding Fab fragment. A computer-assisted method for linker design is described more particularly in Ladner et al., U.S. Pat. Nos. 4,704,692 and 4,881,175, and WO 94/12520.

The in vivo properties of sFv (SCA) polypeptides are different from MAbs and antibody fragments. Due to their small size, sFv (SCA) polypeptides clear more rapidly from the blood and penetrate more rapidly into tissues (Milenic, D. E. et al., *Cancer Research* 51:6363–6371(1991); Colcher et al., *J. Natl. Cancer Inst.* 82:1191 (1990); Yokota et al., *Cancer Research* 52:3402 (1992)). Due to lack of constant regions, sFv (SCA) polypeptides are not retained in tissues such as the liver and kidneys. Due to the rapid clearance and lack of constant regions, sFv (SCA) polypeptides will have low immunogenicity. Thus, sFv (SCA) polypeptides have applications in cancer diagnosis and therapy, where rapid tissue penetration and clearance, and ease of microbial production are advantageous.

A multivalent antigen-binding protein has more than one antigen-binding site. A multivalent antigen-binding protein comprises two or more single-chain protein molecules. Enhanced binding activity, di- and multi-specific binding, and other novel uses of multivalent antigen-binding proteins have been demonstrated. See, Whitlow, M., et al., *Protein Engng.* 7:1017–1026 (1994); Hoogenboom, H. R., *Nature Biotech.* 15:125–126 (1997); and WO 93/11161.

Ladner et al. also discloses the use of the single chain antigen binding molecules in diagnostics, therapeutics, in vivo and in vitro imaging, purifications, and biosensors. The use of the single chain antigen binding molecules in immobilized form, or in detectably labeled forms is also disclosed, as well as conjugates of the single chain antigen binding molecules with therapeutic agents, such as drugs or specific toxins, for delivery to a specific site in an animal, such as a human patient.

Whitlow et al. (*Methods: A Companion to Methods in Enzymology* 2(2):97–105 (June, 1991)) provide a good review of the art of single chain antigen binding molecules and describe a process for making them.

In U.S. Pat. No. 5,091,513, Huston et al. discloses a family of synthetic proteins having affinity for preselected antigens. The contents of U.S. Pat. No. 5,091,513 are incorporated by reference herein. The proteins are characterized by one or more sequences of amino acids constituting a region that behaves as a biosynthetic antibody binding site (BABS). The sites comprise (1) noncovalently associated or disulfide bonded synthetic $V_H$ and $V_L$ regions, (2) $V_H$-$V_L$ or $V_L$-$V_H$ single chains wherein the $V_H$ and $V_L$ are attached to a polypeptide linker, or (3) individual $V_H$ or $V_L$ domains. The binding domains comprises complementarity determining regions (CDRs) linked to framework regions (FRs), which may be derived from separate immunoglobulins.

U.S. Pat. No. 5,091,513 also discloses that three subregions (the CDRs) of the variable domain of each of the heavy and light chains of native immunoglobulin molecules collectively are responsible for antigen recognition and binding. These CDRs consist of one of the hypervariable regions or loops and of selected amino acids or amino acid sequences disposed in the framework regions that flank that particular hypervariable region. It is said that framework regions from diverse species are effective in maintaining CDRs from diverse other species in proper conformation so as to achieve true immunochemical binding properties in a biosynthetic protein.

U.S. Pat. No. 5,091,513 includes a description of a chimeric polypeptide that is a single chain composite polypeptide comprising a complete antibody binding site. This single chain composite polypeptide is described as having a structure patterned after tandem $V_H$ and $V_L$ domains, with a carboxyl terminal of one attached through an amino acid sequence to the amino terminal of the other. It thus comprises an amino acid sequence that is homologous to a portion of the variable region of an immunoglobulin heavy chain ($V_H$) peptide bonded to a second amino acid sequence that was homologous to a portion of the variable region of an immunoglobulin light chain ($V_L$).

The covalent attachment of strands of a polyalkylene glycol to a polypeptide molecule is disclosed in U.S. Pat. No. 4,179,337 to Davis et al., as well as in Abuchowski and Davis "Enzymes as Drugs," Holcenberg and Roberts, Eds., pp. 367–383, John Wiley and Sons, New York (1981). These references disclosed that proteins and enzymes modified with polyethylene glycols have reduced immunogenicity and antigenicity and have longer lifetimes in the bloodstream, compared to the parent compounds. The resultant beneficial properties of the chemically modified conjugates are very useful in a variety of therapeutic applications.

Although amino acid sequences such as the single chain polypeptides described above, and fusion proteins thereof, have not been associated with significant antigenicity in mammals, it has been desirable to prolong the circulating life and even further reduce the possibility of an antigenic response. The relatively small size of the polypeptides and their delicate structure/activity relationship, however, have made polyethylene glycol modification difficult and unpredictable. Most importantly, it was unknown how to modulate retained activity of the polypeptides after conjugation with polymers, such as PEG.

To effect covalent attachment of polyethylene glycol (PEG) or polyalkalene oxides to a protein, the hydroxyl end groups of the polymer must first be converted into reactive functional groups. This process is frequently referred to as "activation" and the product is called "activated PEG" or activated polyalkylene oxide. Methoxy poly(ethylene glycol) (mPEG), capped on one end with a functional group, reactive towards amines on a protein molecule, is used in most cases.

The activated polymers are reacted with a therapeutic agent having nucleophilic functional groups that serve as attachment sites. One nucleophilic functional group commonly used as an attachment site is the E-amino groups of lysines. Free carboxylic acid groups, suitably activated carbonyl groups, oxidized carbohydrate moieties and mercapto groups have also been used as attachment sites.

The hydroxyl group of PEG has been activated with cyanuric chloride and the resulting compound is then coupled with proteins (Abuchowski et al., *J. Biol. Chem.* 252:3578 (1977); Abuchowski & Davis, supra (1981)). However, there are disadvantages in using this method, such as the toxicity of cyanuric chloride and its non-specific reactivity for proteins having functional groups other than amines, such as free essential cysteine or tyrosine residues.

In order to overcome these and other disadvantages, alternative activated PEGs, such as succinimidyl succinate derivatives of PEG ("SS-PEG"), have been introduced (Abuchowski et al., *Cancer Biochem. Biophys.* 7:175–186 (1984)). SS-PEG reacts quickly with proteins (30 minutes) under mild conditions yielding active yet extensively modified conjugates.

Zalipsky, in U.S. Pat. No. 5,122,614, discloses poly (ethylene glycol)-N-succinimide carbonate and its preparation. This form of the polymer is said to react readily with the amino groups of proteins, as well as low molecular weight peptides and other materials that contain free amino groups.

Other linkages between the amino groups of the protein, and the PEG are also known in the art, such as urethane linkages (Veronese et al., *Appl. Biochem. Biotechnol.* 11:141–152 (1985)), carbarnate linkages (Beauchamp et al., *Analyt. Biochem.* 131:25–33 (1983)), and others.

Suzuki et al. (*Biochimica et Biophysica Acta*, 788: 248–255 (1984)) covalently couples immunoglobulin G (IgG) to poly(ethylene glycol) that has previously been activated by cyanuric chloride. The coupled IgG was studied for physicochemical and biological properties such as molecular structure, size-exclusion chromatographic behavior, surface activity, interfacial aggregability, heat aggregability inducing nonspecific complement activation, and antigen-binding activity. The poly(ethylene glycol) coupling to IgG increased the apparent Stokes' radius and the surface activity of IgG and stabilized IgG on heating and/or on exposure to interfaces, while no structural denaturation of IgG was observed. The suppressed nonspecific aggregability was interpreted mainly by difficulty in association between the modified IgG molecules. These results indicated the use of the poly(ethylene glycol)-coupled IgG as an intravenous preparation and also as an additive stabilizing intact IgG for intravenous use.

Sharp et al. (*Analytical Biochemistry* 154: 110–117 (1986)) investigated the possibility of producing biospecific affinity ligands for separating cells in two polymer aqueous phase systems on the basis of cell surface antigens. Rabbit anti-human erythrocyte IgG was reacted with cyanuric chloride-activated monomethyl poly(ethylene glycol) fractions (molecular weights approximately 200, 1900, and 5000) at various molar ratios of PEG to protein lysine groups. The partition coefficient of the protein in a Dextran/PEG two phase system increased with increasing degree of modification and increasing PEG molecular weight. There was a concomitant loss in ability to agglutinate human erythrocytes.

Tullis, in U.S. Pat. No. 4,904,582, describes oligonucleotide conjugates wherein the oligonucleotides are joined through a linking arm to a hydrophobic moiety, which could be a polyalkyleneoxy group. The resulting conjugates are said to be more efficient in membrane transport, so as to be capable of crossing the membrane and effectively modulating a transcriptional system. In this way, the compositions can be used in vitro and in vivo, for studying cellular processes, protecting mammalian hosts from pathogens, and the like.

Excessive polymer conjugation and/or conjugation involving a therapeutic moietie's active site where groups associated with bioactivity are found, however, often result in loss of activity and, thus, therapeutic usefulness. This is often the case with lower molecular weight peptides which have few attachment sites not associated with bioactivity. For example, Benhar et al. (*Bioconjugate Chem.* 5:321–326 (1994)) observed that PEGylation of a recombinant single-chain immunotoxin resulted in the loss of specific target immunoreactivity of the immunotoxin. The loss of activity of the immunotoxin was the result of PEG conjugation at two lysine residues within the antibody-combining region of the immunotoxin. To overcome this problem, Benhar et al. replaced these two lysine residues with arginine residues and were able to obtain an active immunotoxin that was 3-fold more resistant to inactivation by derivatization.

Another suggestion for overcoming these problems discussed above is to use longer, higher molecular weight polymers. These materials, however, are difficult to prepare and expensive to use. Further, they provide little improvement over more readily available polymers.

Another alternative suggested is to attach two strands of polymer via a triazine ring to amino groups of a protein. See, for example, *Enzyme* 26:49–53 (1981) and *Proc. Soc. Exper. Biol. Med.,* 188:364–369(1988). However, triazine is a toxic substance that is difficult to reduce to acceptable levels after conjugation. Thus, non-triazine-based activated polymers would offer substantial benefits to the art.

SUMMARY OF THE INVENTION

The present invention relates to polyalkylene oxide/amino acid sequence conjugates and processes for preparing them. Suitable amino acid sequences are peptides, such as, single chain polypeptides having binding affinity for an antigen, for example, those described by Ladner et al. in U.S. Pat. No. 4,946,778 and Huston et al. in U.S. Pat. No. 5,091,513.

More particularly, the present invention relates to a physiologically active, substantially non-immunogenic polypeptide conjugate containing at least one polyalkylene oxide strand coupled to a single chain polypeptide having binding affinity for an antigen. The single chain polypeptide includes:

(a) a first polypeptide comprising the binding portion of the light chain variable region of an antibody;

(b) a second polypeptide comprising the binding portion of the heavy chain variable region of an antibody; and (c) at least one peptide linker linking said first and second polypeptides (a) and (b) into said single chain polypeptide having binding affinity for the antigen.

In another aspect, the present invention relates to a process for preparing physiologically active, substantially non-immunogenic polypeptide compositions. The process includes coupling a polyalkylene oxide to a single chain polypeptide having the attributes described above. Preferably, the poly(alkylene oxides) used herein are poly(ethylene glycols) that have been activated for coupling to the target polypeptide.

The invention is also directed to a single-chain antigen-binding polypeptide-polyalkylene oxide conjugate, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide-polyalkylene oxide conjugate has an antigen binding affinity within a range of about one-fold to about ten-fold of the antigen binding affinity of the native, unconjugated form of the single-chain antigen-binding polypeptide.

The invention is also directed to a single-chain antigen-binding polypeptide-polyalkylene oxide conjugate, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide-polyalkylene oxide conjugate has an antigen binding affinity within about ten-fold of the antigen binding affinity of the native, unconjugated form of the single-chain antigen-binding polypeptide.

The invention is also directed to a single-chain antigen-binding polypeptide-polyalkylene oxide conjugate, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide-polyalkylene oxide conjugate has an antigen binding affinity within about five-fold of the antigen binding affinity of the native, unconjugated form of the single-chain antigen-binding polypeptide.

The invention is also directed to a single-chain antigen-binding polypeptide-polyalkylene oxide conjugate, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide-polyalkylene oxide conjugate has an antigen binding affinity within about two-fold of the antigen binding affinity of the native, unconjugated form of the single-chain antigen-binding polypeptide.

The invention is also directed to a single-chain antigen-binding polypeptide capable of polyalkylene oxide conjugation, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide has at least one Cys residue wherein the Cys residue is capable of polyalkylene oxide conjugation and the Cys residue is located at a position selected from the group consisting of (i) the amino acid position 11, 12, 13, 14 or 15 of the light chain variable region; (ii) the amino acid position 77, 78 or 79 of the light chain variable region; (iii) the amino acid position 11, 12, 13, 14 or 15 of the heavy chain variable region; (iv) the amino acid position 82B, 82C or 83 of the heavy chain variable region; (v) any amino acid position of the peptide linker; (vi) adjacent to the C-terminus of polypeptide (a) or (b); and (vii) combinations thereof, wherein the polyalkylene oxide conjugated single-chain antigen-binding polypeptide is capable of binding an antigen.

The invention is also directed to a single-chain antigen-binding polypeptide capable of polyalkylene oxide conjugation, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide has at least three consecutive Lys residues wherein the consecutive Lys residues are capable of polyalkylene oxide conjugation and any one of the consecutive Lys residues is located at a position selected from the group consisting of (i) any amino acid position of the peptide linker; (ii) adjacent to the C-terminus of polypeptide (a) or (b); and (iii) combinations thereof, wherein the polyalkylene oxide conjugated single-chain antigen-binding polypeptide is capable of binding an antigen. These consecutive lysine residues in the sFv (SCA) protein (i.e., oligo-lysine sFv) generate a "hot spot" for polyalkylene oxide conjugation.

The invention is also directed to a single-chain antigen-binding polypeptide capable of polyalkylene oxide conjugation, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide has at least two consecutive Cys residue wherein the consecutive Cys residues are capable of polyalkylene oxide conjugation and any one of the consecutive Cys residues is located at a position selected from the group consisting of (i) any amino acid position of the peptide linker; (ii) adjacent to the C-terminus of polypeptide (a) or (b); and (iii) combinations thereof, wherein the polyalkylene oxide conjugated single-chain antigen-binding polypeptide is capable of binding an antigen. These consecutive cysteine residues in the sFv (SCA) protein (i.e., oligo-cysteine sFv) generate a "hot spot" for polyalkylene oxide conjugation.

The invention is further directed to a genetic sequence encoding a single-chain antigen-binding polypeptide capable of polyalkylene oxide conjugation, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide has at least one Cys residue wherein the Cys residue is capable of polyalkylene oxide conjugation and the Cys residue is located at a position selected from the group consisting of (i) the amino acid position 11, 12, 13, 14 or 15 of the light chain variable region; (ii) the amino acid position 77, 78 or 79 of the light chain variable region; (iii) the amino acid position 11, 12, 13, 14 or 15 of the heavy chain variable region; (iv) the amino acid position 82B, 82C or 83 of the heavy chain variable region; (v) any amino acid position of the peptide linker; (vi) adjacent to the C-terminus of polypeptide (a) or (b); and (vii) combinations thereof, wherein the polyalkylene oxide conjugated single-chain antigen-binding polypeptide is capable of binding an antigen.

The invention is further directed to a genetic sequence encoding a single-chain antigen-binding polypeptide capable of polyalkylene oxide conjugation, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide has at least three consecutive Lys residue wherein the consecutive Lys residues are capable of polyalkylene oxide conjugation and any one of the consecutive Lys residues is located at a position selected from the group consisting of (i) any amino acid position of the peptide linker; (ii) adjacent to the C-terminus of polypeptide (a) or (b); and (iii) combinations thereof, wherein the polyalkylene oxide conjugated single-chain antigen-binding polypeptide is capable of binding an antigen. These consecutive lysine residues in the sFv (SCA) protein (i.e., oligo-lysine sFv) generate a "hot spot" for polyalkylene oxide conjugation.

The invention is further directed to a genetic sequence encoding a single-chain antigen-binding polypeptide capable of polyalkylene oxide conjugation, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide has at least two consecutive Cys residue wherein the consecutive Cys residues are capable of polyalkylene oxide conjugation and any one of the consecutive Cys residues is located at a position selected from the group consisting of (i) any amino acid position of the peptide linker; (ii) adjacent to the C-terminus of polypeptide (a) or (b); and (iii) combinations thereof, wherein the polyalkylene oxide conjugated single-chain antigen-binding polypeptide is capable of binding an antigen. These consecutive cysteine residues in the sFv (SCA) protein (i.e., oligo-cysteine sFv) generate a "hot spot" for polyalkylene oxide conjugation.

The genetic sequence may be DNA or RNA.

The invention is directed to a replicable cloning or expression vehicle comprising the above described DNA sequence. The invention is also directed to such vehicle which is a plasmid. The invention is further directed to a host cell transformed with the above described DNA. The host cell may be a bacterial cell, a yeast cell or other fungal cell, an insect cell or a mammalian cell line. A preferred host is *Pichia pastoris*.

The invention is directed to a method of producing a single-chain antigen-binding polypeptide capable of polyalkylene oxide conjugation, comprising:

(a) providing a first genetic sequence encoding a first polypeptide comprising the antigen binding portion of the variable region of an antibody heavy or light chain;

(b) providing a second genetic sequence encoding a second polypeptide comprising the antigen binding portion of the variable region of an antibody heavy or light chain; and (c) linking the first and second genetic sequences (a) and (b) with a third genetic sequence encoding a peptide linker into a fourth genetic sequence encoding a single chain polypeptide having an antigen binding site, wherein the single-chain antigen-binding polypeptide has at least one Cys residue wherein the Cys residue is capable of polyalkylene oxide conjugation and the Cys residue is located at a position selected from the group consisting of(i) the amino acid position 11, 12, 13, 14 or 15 of the light chain variable region; (ii) the amino acid position 77, 78 or 79 of the light chain variable region; (iii) the amino acid position 11, 12, 13, 14 or 15 of the heavy chain variable region; (iv) the amino acid position 82B, 82C or 83 of the heavy chain variable region; (v) any amino acid position of the peptide linker; (vi) adjacent to the C-terminus of polypeptide (a) or (b); and (vii) combinations thereof, wherein the polyalkylene oxide conjugated single-chain antigen-binding polypeptide is capable of binding an antigen;

(d) transforming a host cell with the fourth genetic sequence encoding a single-chain antigen-binding polypeptide of (c); and (e) expressing the single-chain antigen-binding polypeptide of (c) in the host, thereby producing a single-chain antigen-binding polypeptide capable of polyalkylene oxide conjugation.

The invention is further directed to a multivalent single-chain antigen-binding protein, comprising two or more single-chain antigen-binding polypeptides, each single-chain antigen-binding polypeptide comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide has at least one Cys residue wherein the Cys residue is capable of polyalkylene oxide conjugation and the Cys residue is located at a position selected from the group consisting of (i) the amino acid position 11, 12, 13, 14 or 15 of the light chain variable region; (ii) the amino acid position 77, 78 or 79 of the light chain variable region; (iii) the amino acid position 11, 12, 13, 14 or 15 of the heavy chain variable region; (iv) the amino acid position 82B, 82C or 83 of the heavy chain variable region; (v) any amino acid position of the peptide linker; (vi) adjacent to the C-terminus of polypeptide (a) or (b); and (vii) combinations thereof, wherein the polyalkylene oxide conjugated single-chain antigen-binding polypeptide is capable of binding an antigen.

In the above described embodiments of the invention, the Cys polyalkylene oxide conjugation sequence may be capable of attaching a polyalkylene oxide moiety and the Cys residue is located at a position selected from the group consisting of (i') the amino acid position 77 of the light chain variable region; (ii') the amino acid position 82B of the heavy chain variable region; (iii') the amino acid position 3 of the peptide linker; (iv') adjacent to the C-terminus of polypeptide (a) or (b); (v') N-terminus and C-terminus; and (vi') combinations thereof, wherein the polyalkylene oxide conjugated single-chain antigen-binding polypeptide is capable of binding an antigen.

In the above described embodiments of the invention, the oligo-Lys polyalkylene oxide conjugation sequence may be capable of attaching a polyalkylene oxide moiety at the oligo-Lys residues located adjacent to the C-terminus of the protein, wherein the polyalkylene oxide conjugated single-chain antigen-binding polypeptide is capable of binding an antigen.

In the above described embodiments of the invention, the C-terminus of the second polypeptide (b) may be the native C-terminus. The C-terminus of the second polypeptide (b) may comprise a deletion of one or plurality of amino acid residue(s), such that the remaining N-terminus amino acid residues of the second polypeptide are sufficient for the polyalkylene oxide conjugated polypeptide to be capable of binding an antigen. The C-terminus of the second polypeptide may comprise an addition of one or plurality of amino acid residue(s), such that the polyalkylene oxide conjugated polypeptide is capable of binding an antigen.

In a preferred embodiment of the invention, the first polypeptide (a) may comprise the antigen binding portion of the variable region of an antibody light chain and the second polypeptide (b) comprises the antigen binding portion of the variable region of an antibody heavy chain.

The invention is also directed to a method of detecting an antigen suspected of being in a sample, comprising:

(a) contacting the sample with the polyalkylene oxide conjugated polypeptide or protein of the invention, wherein the polyalkylene oxide conjugated polypeptide is conjugated to one or plurality of detectable label molecule(s), or conjugated to a carrier having one or plurality of detectable label molecule(s) bound to the carrier; and (b) detecting whether the polyalkylene oxide conjugated single-chain antigen-binding polypeptide has bound to the antigen.

The invention is further directed to a method of imaging the internal structure of an animal, comprising administering to the animal an effective amount of the polyalkylene oxide conjugated polypeptide or protein of the invention, wherein the polyalkylene oxide conjugated polypeptide is conjugated to one or plurality of detectable label or chelator molecule(s), or conjugated to a carrier having one or plurality of detectable label or chelator molecule(s) bound to the carrier, and measuring detectable radiation associated with the animal. Animal includes human and nonhuman.

The invention is also directed to a method for treating a targeted disease, comprising administering an effective amount of a composition comprising the polyalkylene oxide conjugated polypeptide or protein of the invention and a pharmaceutically acceptable carrier vehicle, wherein the polyalkylene oxide conjugated polypeptide is conjugated to one or plurality of bioactive molecules, such as peptides, lipids, nucleic acids (i.e., phosphate-lysine complexes), drug, toxin, boron addend or radioisotope molecule(s), or conjugated to a carrier having one or plurality of peptides, lipids, nucleic acids (i.e., phosphate-lysine complexes), drug, toxin, boron addend or radioisotope molecule(s) bound to the carrier.

BRIEF DESCRIPTION OF THE DRAWINGS

FIGS. 2A and 2B show the DNA and protein sequence of CC49/218 SCA which has four engineered cysteine residues at the positions indicated by the codons underlined and marked by an asterisk. Also highlighted are the CDR sequences (double underlined) and the 218 linker (underlined and labeled). In addition, there are four natural cysteine residues in the protein which are involved in two disulfide bonds. These are not underlined. The four engineered cysteine residues occur independently in four different mutants currently, but may be combined in the exact four-mutant codon version shown in these figures.

FIGS. 3A and 3B show the DNA and protein sequence of CC49/218 SCA with an engineered oligo-lysine C-terminal tail segment. The eight new lysine residues were genetically engineered at a BstEII site and are shown underlined and marked with asterisks. Also highlighted are the CDR sequences (double underlined), the 218 linker (underlined and labeled) and selected restriction sites.

DESCRIPTION OF THE EMBODIMENTS

Figure 1:
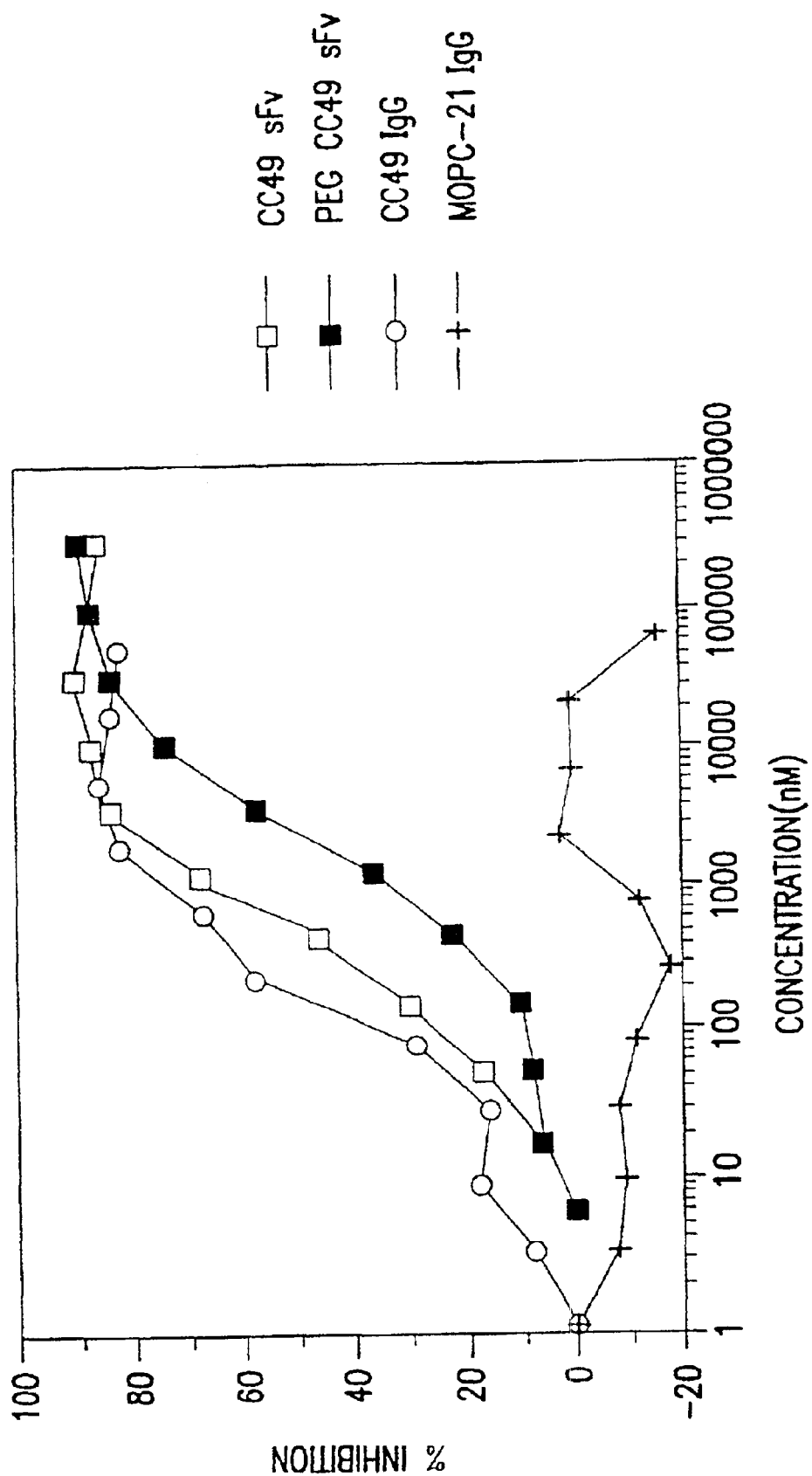
FIG. 1 is a graphical representation of three competition ELISA's in which unlabeled PEG modified CC49/212 SCA (closed squares), CC49/212 SCA (open squares), CC49 IgG (open circles), and MOPC-21 IgG (+) competed against a CC49 IgG radiolabeled with $^{125}$I for binding to the TAG-72 antigen on a human breast carcinoma extract.

The present invention is directed to the novel combination of a polyalkylene glycol and a single chain polypeptide having binding affinity for an antigen, the polyalkylene glycol and polypeptide preferably being joined together by means of a coupling agent.

Single Chain Polypeptides

The invention relates to the discovery that polyalkylene oxide conjugated single-chain antigen-binding proteins ("SCA") or single-chain variable fragments of antibodies ("sFv"), such as PEGylated SCA proteins, have significant utility beyond that of the nonPEGylated single-chain antigen-binding proteins. In addition to maintaining an antigen binding site, a PEGylated SCA protein has a PEG moiety which reduces antigenicity and increases the half life of the modified polypeptide in the bloodstream. Accordingly, the invention is directed to monovalent and multivalent SCA proteins capable of PEGylation, compositions of monovalent and multivalent PEGylated SCA proteins, methods of making and purifying monovalent and multivalent PEGylated SCA proteins, and uses for PEGylated SCA proteins. The invention is also directed to PEGylated SCA proteins having a diagnostic or therapeutic agent covalently attached to an Cys-linked PEGylated polypeptide or an oligo-Lys linked PEGylated polypeptide.

The terms "single-chain antigen-binding molecule" (SCA) or "single-chain Fv" (sFv) are used interchangeably. They are structurally defined as comprising the binding portion of a first polypeptide from the variable region of an antibody $V_L$ (or $V_H$), associated with the binding portion of a second polypeptide from the variable region of an antibody $V_H$ (or $V_L$), the two polypeptides being joined by a peptide linker linking the first and second polypeptides into a single polypeptide chain, such that the first polypeptide is N-terminal to the linker and second polypeptide is C-terminal to the first polypeptide and linker. The single polypeptide chain thus comprises a pair of variable regions connected by a polypeptide linker. The regions may associate to form a functional antigen-binding site, as in the case wherein the regions comprise a light-chain and a heavy-chain variable region pair with appropriately paired complementarity determining regions (CDRs). In this case, the single-chain protein is referred to as a "single-chain antigen-binding protein" or "single-chain antigen-binding molecule."

Single-chain Fvs can and have been constructed in several ways. Either $V_L$ is the N-terminal domain followed by the linker and $V_H$ (a $V_L$-Linker-$V_H$ construction) or $V_H$ is the N-terminal domain followed by the linker and $V_L$ ($V_H$-Linker-$V_L$ construction). The preferred embodiment contains $V_L$ in the N-terminal domain (see, Anand, N. N., et al., J. Biol. Chem. 266:21874–21879 (1991)). Alternatively, multiple linkers have also been used. Several types of sFv (SCA) proteins have been successfully constructed and purified, and have shown binding affinities and specificities similar to the antibodies from which they were derived.

A description of the theory and production of single-chain antigen-binding proteins is found in Ladner et al., U.S. Pat.

Nos. 4,946,778, 5,260,203, 5,455,030 and 5,518,889, and in Huston et al., U.S. Pat. No. 5,091,513 ("biosynthetic antibody binding sites" (BABS)), all incorporated herein by reference. The single-chain antigen-binding proteins produced under the process recited in the above patents have binding specificity and affinity substantially similar to that of the corresponding Fab fragment.

Typically, the Fv domains have been selected from the group of monoclonal antibodies known by their abbreviations in the literature as 26-10, MOPC 315, 741F8, 520C9, McPC 603, D1.3, murine phOx, human phOx, RFL3.8 sTCR, 1A6, Se155-4, 18-2-3, 4-4-20, 7A4-1, B6.2, CC49, 3C2, 2c, MA-15C5/$K_{12}G_0$, Ox, etc. (see, Huston, J. S. et al., *Proc. Natl. Acad. Sci. USA* 85:5879–5883 (1988); Huston, J. S. et al., *SIM News* 38(4) (Supp):11 (1988); McCartney, J. et al., *ICSU Short Reports* 10:114 (1990); McCartney, J. E. et al., unpublished results (1990); Nedelman, M. A. et al., *J. Nuclear Med.* 32 (Supp.):1005 (1991); Huston, J. S. et al., In: *Molecular Design and Modeling: Concepts and Applications, Part B*, edited by J. J. Langone, *Methods in Enzymology* 203:46–88 (1991); Huston, J. S. et al., In: *Advances in the Applications of Monoclonal Antibodies in Clinical Oncology*, Epenetos, A. A. (Ed.), London, Chapman & Hall (1993); Bird, R. E. et al., *Science* 242:423–426 (1988); Bedzyk, W. D. et al., *J. Biol. Chem.* 265:18615–18620 (1990); Colcher, D. et al., *J. Nat. Cancer Inst.* 82:1191–1197 (1990); Gibbs, R. A. et al., *Proc. Natl. Acad. Sci. USA* 88:4001–4004 (1991); Milenic, D. E. et al., *Cancer Research* 51:6363–6371 (1991); Pantoliano, M. W. et al., *Biochemistry* 30:10117–10125 (1991); Chaudhary, V. K. et al., *Nature* 339:394–397 (1989); Chaudhary, V. K. et al., *Proc. Natl. Acad. Sci. USA* 87:1066–1070 (1990); Batra, J. K. et al., *Biochem. Biophys. Res. Comm.* 171:1–6 (1990); Batra, J. K. et al., *J. Biol. Chem.* 265:15198–15202 (1990); Chaudhary, V. K. et al., *Proc. Natl. Acad Sci. USA* 87:9491–9494 (1990); Batra, J. K. et al., *Mol. Cell. Biol.* 11:2200–2205 (1991); Brinkmann, U. et al., *Proc. Natl. Acad. Sci. USA* 88:8616–8620 (1991); Seetharam, S. et al., *J. Biol. Chem.* 266:17376–17381 (1991); Brinkmann, U. et al., *Proc. Natl. Acad. Sci. USA* 89:3075–3079 (1992); Glockshuber, R. et al., *Biochemistry* 29:1362–1367 (1990); Skerra, A. et al., *Bio/Technol.* 9:273–278 (1991); Pack, P. et al., *Biochemistry* 31:1579–1534 (1992); Clackson, T. et al., *Nature* 352:624–628 (1991); Marks, J. D. et al., *J. Mol. Biol.* 222:581–597 (1991); Iverson, B. L. et al., *Science* 249:659–662 (1990); Roberts, V. A. et al., *Proc. Natl. Acad. Sci. USA* 87:6654–6658 (1990); Condra, J. H. et al., *J. Biol. Chem.* 265:2292–2295 (1990); Laroche, Y. et al., *J. Biol. Chem.* 266:16343–16349 (1991); Holvoet, P. et al., *J. Biol. Chem.* 266:19717–19724 (1991); Anand, N. N. et al., *J. Biol. Chem.* 266:21874–21879 (1991); Fuchs, P. et al., *Biol Technol.* 9:1369–1372 (1991); Breitling, F. et al., *Gene* 104:104–153 (1991); Seehaus, T. et al., *Gene* 114:235–237 (1992); Takkinen, K. et al., *Protein Engng.* 4:837–841 (1991); Dreher, M. L. et al., *J. Immunol. Methods* 139:197–205 (1991); Mottez, E. et al., *Eur. J. Immunol.* 21:467–471 (1991); Traunecker, A. et al., *Proc. Natl. Acad. Sci. USA* 88:8646–8650 (1991); Traunecker, A. et al., *EMBO J.* 10:3655–3659 (1991); Hoo, W. F. S. et al., *Proc. Natl. Acad. Sci. USA* 89:4759–4763 (1993)).

Linkers of the invention used to construct sFv (SCA) polypeptides are designed to span the C-terminus of $V_L$ (or neighboring site thereof) and the N-terminus of $V_H$ (or neighboring site thereof) or between the C-terminus of $V_H$ and the N-terminus of $V_L$. The preferred length of the peptide linker should be from 2 to about 50 amino acids. In each particular case, the preferred length will depend upon the nature of the polypeptides to be linked and the desired activity of the linked fusion polypeptide resulting from the linkage. Generally, the linker should be long enough to allow the resulting linked fusion polypeptide to properly fold into a conformation providing the desired biological activity. Where conformational information is available, as is the case with sFv (SCA) polypeptides discussed below, the appropriate linker length may be estimated by consideration of the 3-dimensional conformation of the substituent polypeptides and the desired conformation of the resulting linked fusion polypeptide. Where such information is not available, the appropriate linker length may be empirically determined by testing a series of linked fusion polypeptides with linkers of varying lengths for the desired biological activity. Such linkers are described in detail in WO 94/12520, incorporated herein by reference.

Preferred linkers used to construct sFv (SCA) polypeptides have between 10 and 30 amino acid residues. The linkers are designed to be flexible, and it is recommended that an underlying sequence of alternating Gly and Ser residues be used. To enhance the solubility of the linker and its associated single chain Fv protein, three charged residues may be included, two positively charged lysine residues (K) and one negatively charged glutamic acid residue (E). Preferably, one of the lysine residues is placed close to the N-terminus of $V_H$, to replace the positive charge lost when forming the peptide bond of the linker and the $V_H$. Such linkers are described in detail in U.S. patent application Ser. No. 08/224,591, filed Apr. 7, 1994, incorporated herein by reference. See also, Whitlow, M., et al., *Protein Engng.* 7:1017–1026(1994).

For multivalent sFvs (SCA), the association of two or more sFvs (SCA) is required for their formation. Although, multivalent sFvs (SCA) can be produced from sFvs (SCA) with linkers as long as 25 residues, they tend to be unstable. Holliger, P., et al., *Proc. Natl. Acad. Sci. USA* 90:6444–6448 (1993), have recently demonstrated that linkers 0 to 15 residues in length facilitate the formation of divalent Fvs. See, Whitlow, M., et al., *Protein Engng.* 7:1017–1026 (1994); Hoogenboom, H. R., *Nature Biotech.* 15:125–126 (1997); and WO 93/11161.

An object of the present invention is to produce a single-chain antigen-binding polypeptide-polyalkylene oxide conjugate which retains antigen binding affinity within a range of about two-fold to about ten-fold of the antigen binding affinity of the native single-chain antigen-binding polypeptide.

Another object of the present invention is to produce an sFv (SCA) having one or more Cys residues such that the Cys residue is capable of being conjugated with PEG and the PEGylated polypeptide is capable of binding an antigen (i.e., the PEGylated polypeptide's ability to bind an antigen is not disrupted). A further object of the present invention is to produce an sFv (SCA) having three or more consecutive Lys residues such that the Lys residues are capable of being conjugated with PEG and the PEGylated polypeptide is capable of binding an antigen (i.e., the PEGylated polypeptide's ability to bind an antigen is not disrupted). These novel sFv (SCA) proteins may be conjugated to activated polyethylene glycol (PEG) such that the PEG modification occurs only (or preferentially) at the specifically engineered sites. The activated PEG molecules would be thiol-reactive or amine-reactive polymers such as are well known in the art. The designed changes correspond to amino acid residues on the sFv (SCA) surface which are well separated spatially from the antigen-binding site as deduced from known three-dimentional models of the antibody Fv domain.

A further object of the invention is to produce monovalent and multivalent sFvs (SCA) having one or more Cys PEG conjugation sequence(s). A further object of the invention is to produce monovalent and multivalent sFvs (SCA) having three or more consecutive Lys (i.e., oligo-Lys) PEG conjugation sequence(s). For multivalent sFv (SCA), the association of two or more sFvs (SCAs) is required for their formation. For example, multivalent sFvs (SCAs) may be generated by chemically crosslinking two sFvs (SCAs) with C-terminal cysteine residues (Cumber et al., *J. Immunol.* 149:120–126 (1992)) and by linking two sFvs (SCAs) with a third polypeptide linker to form a dimeric Fv (SCA) (George et al., *J. Cell. Biochem.* 15E:127 (1991)). Details for producing multivalent sFvs (SCAs) by aggregation are described in Whitlow, M., et al., *Protein Engng.* 7:1017–1026 (1994). Multivalent antigen-binding fusion proteins of the invention can be made by any process, but preferably according to the process for making multivalent antigen-binding proteins set forth in WO 93/11161, incorporated herein by reference.

Identification and Synthesis of Site Specific PEGylation Sequences

In the present invention, Cys PEGylation sites may occur in the $V_L$ and $V_H$ regions, adjacent to the C-terminus of the polypeptide ($V_L$, $V_H$ or neighboring site thereof), the N-terminus of the polypeptide ($V_L$, $V_H$ or neighboring site thereof), the linker region between the first and second polypeptide regions, or occur in a combination of these regions. In the present invention, oligo-Lys PEGylation sites may occur in the polypeptide linker or in the C-terminus or adjacent to the C-terminus of the polypeptide. The design of the PEG conjugaton sites on a protein involves examining the structural information known about the protein and the residues in the proteins involved in antigen binding. The PEG conjugaton sites are chosen to be as far from these residues as possible so as to prevent disruption of the antigen-binding site.

The Cys or the oligo-Lys PEGylation site may occur in (1) the native C-terminus of $V_L$ (or $V_H$), (2) the C-terminus of $V_L$ (or $V_H$) wherein the C-terminus has a deletion of one or plurality of amino acid residue(s), such that the remaining N-terminus amino acid residues of the peptide are sufficient for the PEGylated polypeptide to be capable of binding an antigen or (3) the C-terminus of $V_L$ (or $V_H$) wherein the C-terminus has an addition of one or plurality of amino acid residue(s), such that the remaining N-terminus amino acid residues of the peptide are sufficient for the PEGylated polypeptide to be capable of binding an antigen. By "native" is intended the naturally occurring C-terminus of the immunoglobulin (first or second polypeptide). By "C-terminus" it is well understood in the art as intending the C-terminal amino acid residue or the C-terminal region of the polypeptide, which could include up to all of the amino acid residues of the polypeptide excluding the first N-terminal amino acid residue of the polypeptide. However, in the present invention, "C-terminus" is intended as the C-terminal amino acid residue of the above mentioned three types of C-terminus (1, 2, or 3), unless otherwise indicated or intended.

PEGylation sites were identified and engineered at residues within loop sites in regions of the sFv (SCA) that are diametrically opposed to the antigen binding site. The five loop regions and C-terminal extension chosen as preferred sites of glycosylation are among the most distant regions spatially removed from the binding site.

The six furthest portions of an sFv (SCA) from the antigen binding site are as follows:
1) The loop made up of residues 11 to 15 in the light chain;
2) The loop made up of residues 77 to 79 in the light chain;
3) The N-terminus of the linker;
4) The loop made up of residues 11 to 15 in the heavy chain;
5) The loop made up of residues 82B, 82C and 83 in the heavy chain; and
6) The C-terminus of the sFv (or SCA).

The residues are identified as according to Kabat et al., *Sequences of Proteins of Immunological Interest*, 5th ed., U.S. Dept. Health and Human Services, Bethesda, Md. (1991). These possible PEGylation sites were determined by examining the 4-4-20 mouse Fab structure (see, Whitlow, M. et al., *Protein Engng* 8:749–761 (1995), incorporated herein by reference).

After identifying the loops furthest from the antigen binding site, the nucleic and amino acid sequences of each loop are examined for possible Cys PEGylation sites that may be engineered into the loop region. The engineered placement of the Cys residue anywhere in these six identified regions can generate a preferred site for sFv (SCA) PEGylation. The engineered placement of the oligo-Lys residues in the linker, the C-terminus of the sFv (SCA) and/or adjacent to the C-terminus of the sFv (SCA) can generate a preferred site for sFv PEGylation.

The design approach described above has been used for the CC49/218 SCA. FIGS. 2A and 2B show the following resulting designs: designed PEGylation site no. 1 in the light chain of the CC49/218 SCA; designed PEGylation site no. 2 in the N-terminal end of the linker in CC49/218 SCA; designed PEGylation site no. 3 in the heavy chain of the CC49/218 SCA; designed PEGylation site no. 4 at the C-terminus of the CC491218 SCA. FIGS. 3A and 3B show the following resulting designs: designed oligo-Lys "hot spot" PEGylation sites at the C-terminus of the CC49/218 SCA. Any combination of these sites could be used.

The particular nucleotide sequence which is used to introduce a Cys or oligo-Lys PEGylation site into the various positions will depend upon the naturally-occurring nucleotide sequence. The most preferred sites are those in which it takes a minimum number of changes to generate the PEGylation site. Of course, based on the redundancy of the genetic code, a particular amino acid may be encoded by multiple nucleotide sequences.

Site-directed mutagenesis is used to change the native protein sequence to one that incorporates the Cys residue or oligo-Lys residues for PEGylation. The mutant protein gene is placed in an expression system, such as bacterial cells, yeast or other fungal cells, insect cells or mammalian cells. The mutant protein can be purified by standard purification methods.

Oligonucleotide-directed mutagenesis methods for generating the Cys or oligo-Lys PEGylation sites and related techniques for mutagenesis of cloned DNA are well known in the art. See, Sambrook et al., MOLECULAR CLONING: A LABORATORY MANUAL, 2nd ed., Cold Spring Harbor Laboratory, Cold Spring Harbor, N.Y. (1989); Ausubel et al. (eds.), CURRENT PROTOCOLS IN MOLECULAR BIOLOGY, John Wiley and Sons (1987), both incorporated herein by reference. A preferred oligonucleotide-directed mutagenesis method for the present invention is according to Ho et al., *Gene* 77:51–59 (1989), incorporated herein by reference.

Hosts and Vectors

After mutating the nucleotide sequence of the sFv (SCA), the mutated DNA can be inserted into a cloning vector for further analysis, such as for confirmation of the DNA sequence. To express the polypeptide encoded by the mutated DNA sequence, the DNA sequence is operably linked to regulatory sequences controlling transcriptional expression and introduced into either a prokaryotic or eukaryotic host cell.

Although sFvs (SCAs) are typically produced by prokaryotic host cells, eukaryotic host cells are the preferred host cells. Preferred host cells include yeast or other fungal cells, insect cells or mammalian cells. Standard protein purification methods may be used to purify these mutant proteins. Only minor modification to the native protein's purification scheme may be required.

Also provided by the invention are DNA molecules such as purified genetic sequences or plasmids or vectors encoding the sFv (SCA) of the invention that have engineered Cys residues and/or oligo-Lys residues capable of PEG conjugation. The DNA sequence for the PEGylated sFv (SCA) polypeptide can be chosen so as to optimize production in organisms such as prokaryotes, yeast or other fungal cells, insect cells or mammalian cells.

The DNA molecule encoding an sFv (SCA) having Cys residues and/or oligo-Lys residues for PEG conjugation can be operably linked into an expression vector and introduced into a host cell to enable the expression of the engineered sFv (SCA) protein by that cell. A DNA sequence encoding an sFv (SCA) having Cys and/or oligo-Lys PEGylation sites may be recombined with vector DNA in accordance with conventional techniques. Recombinant hosts as well as methods of using them to produce single chain proteins of the invention are also provided herein.

The expression of such sFv (SCA) proteins of the invention can be accomplished in procaryotic cells. Preferred prokaryotic hosts include, but are not limited to, bacteria such as Neisseria, Mycobacteria, Streptococci, Chlamydia and *E. coli.*

Eukaryotic hosts for cloning and expression of such sFv (SCA) proteins of the invention include insect cells, yeast, fungi, and mammalian cells (such as, for example, human or primate cells) either in vivo, or in tissue culture. A preferred host for the invention is *Pichia pastoris*.

The appropriate DNA molecules, hosts, methods of production, isolation and purification of monovalent, multivalent and fusion forms of proteins, especially sFv (SCA) polypeptides, are thoroughly described in the prior art, such as, e.g., U.S. Pat. No. 4,946,778, which is fully incorporated herein by reference.

The sFv (SCA) encoding sequence having Cys residues and/or oligo-Lys residues for PEG conjugation and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired sFv (SCA) protein may occur through the transient expression of the introduced sequence. Alternatively, permanent expression may occur through the integration of the introduced sFv (SCA) sequence into the host chromosome.

In one embodiment, the sFv (SCA) sequence can be integrated into the host cell chromosome. Cells which have stably integrated the introduced DNA into their chromosomes can be selected by also introducing one or more markers which allow for selection of host cells which contain the sFv (SCA) sequence and marker. The marker may complement an auxotrophy in the host (such as his4, leu2, or ura3, which are common yeast auxotrophic markers), biocide resistance, e.g., antibiotics, or resistance to heavy metals, such as copper, or the like. The selectable marker gene can either be directly linked to the sFv (SCA) DNA sequence to be expressed, or introduced into the same cell by co-transfection.

In another embodiment, the introduced sequence will be incorporated into a plasmid vector capable of autonomous replication in the recipient host cell. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast vector systems can be utilized. Examples of such expression vectors include the yeast 2-micron circle, the expression plasmids YEP13, YCP and YRP, etc., or their derivatives. Such plasmids are well known in the art (Botstein et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445-470 (1981); Broach, J. R., *Cell* 28:203–204 (1982)).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototrophy to an auxotrophic host, biocide resistance, e.g., antibiotics, or resistance to heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.* 3:280 (1983), and others.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Preferred vectors for expression in Pichia are pHIL-S 1 (Invitrogen Corp.) and pPIC9 (Invitrogen Corp.). Other suitable vectors will be readily apparent to the skilled artisan.

Once the vector or DNA sequence containing the constructs has been prepared for expression, the DNA constructs may be introduced or transformed into an appropriate host. Various techniques may be employed, such as transformation, transfection, protoplast fusion, calcium phosphate precipitation, electroporation, or other conventional techniques. After the cells have been transformed with the recombinant DNA (or RNA) molecule, the cells are grown in media and screened for appropriate activities. Expression of the sequence results in the production of the mutant sFv (SCA) for PEG conjugation of the present invention.

Straight Chain Polymers

The straight chain polyalkylene glycols employed in the practice of the present invention are of the structural formula

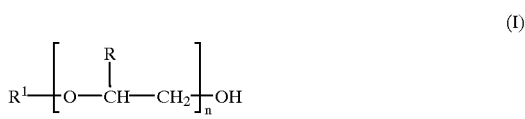

(I)

wherein R is selected from the group consisting of hydrogen, lower alkyl and mixtures thereof, $R^1$ is selected from the group consisting of hydrogen and lower alkyl, and n is a positive integer. By "lower alkyl" is meant an alkyl group having from one to four carbon atoms, i.e., methyl, ethyl, propyl, butyl, and isomers of the foregoing. R is preferably selected from the group consisting of hydrogen, methyl, and mixtures thereof, $R^1$ is preferably selected from the group consisting of hydrogen and methyl, and n is preferably a positive integer of 500 or less. R is most preferably hydrogen, $R^1$ is most preferably methyl, and n is most preferably an integer of 7 to 150. It will be readily apparent to those skilled in the art that the preferred poly(alkylene glycols) employed in the practice of the present invention are poly(ethylene glycol), poly(propylene glycol), mixtures thereof, and copolymers of poly(ethylene glycol) and poly(propylene glycol), wherein one of the terminal hydroxyl groups of the polymer may be substituted with a lower alkyl group. A preferred polyalkylene glycol for use in the present invention is poly(ethylene glycol)-hydrazine. The most preferred polyalkylene glycol for use in the present invention is methoxy poly(ethylene glycol).

Hereinafter, for convenience, the polyalkylene glycol employed in the practice of the present invention will be designated PAG, which term is intended to include both compounds wherein $R^1$ is hydrogen and compounds wherein $R^1$ is alkyl. PEG refers to poly(ethylene glycol) and mPEG refers to methoxy poly(ethylene glycol).

The PAG does not have to be of a particular molecular weight, but it is preferred that the molecular weight be between about 500 and about 40,000; more preferably, between about 2,000 and about 20,000. The choice of molecular weight of PAG is made based on the nature of the particular polypeptide employed, for example, the number of amino or other groups available on the polypeptide for modification. Molecular weights of about 10,000 and about 20,000 are most preferred.

It is well known in the art that PAGs that contain two terminal hydroxyl groups per moiety are capable of crosslinking other polymers, e.g. proteins. Where, as is often the case, crosslinking would be deemed undesirable, such crosslinking can be minimized or prevented by means known in the art. For example, Davis et al. in U.S. Pat. No. 4,179,337 have pointed out that a preferred means for preventing crosslinking is to preblock one end of the PAG, such as is done in the commercially available methoxy poly(ethylene glycol).

The PAGs employed in the practice of the present invention are preferably coupled to polypeptides by means of suitable coupling agents. A useful review of a number of coupling agents that can be employed in the practice of the present invention appears in Dreborg et al., *Critical Reviews in Therapeutic Drug Carrier Systems* 6(4):315–365 (1990), see, especially, pp. 317–320.

Probably the best known coupling agent for this purpose is cyanuric chloride. Its use has been described in numerous references, see, for example, Abuchowski et al., *J. Biol. Chem.* 252(11):3578–3581 (Jun. 10, 1977).

Zalipsky et al., *Eur. Pol. J.* 19(12): 1177–1183 (1983), among others, have described the reaction of methoxy poly(ethylene glycol) with succinic anhydride:

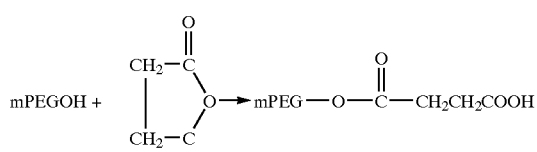

It is also known to alkylate mPEG with ethylbromoacetate in the presence of a base such as K-tertiary butoxide in tertiary butanol, Na-naphthalene in tetrahydrofuran, or butyl lithium in benzene:

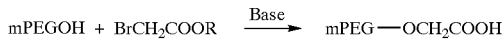

The terminal hydroxyl groups of PEG can be transformed into amine, carboxyl, or hexamethyl isocyanate groups. See, for example, Zalipsky et al., 1983, supra. A mixed anhydride derivative of carboxylated mPEG can be prepared in the presence of triethylamine and then reacted with proteins:

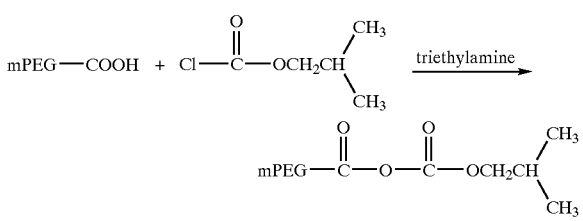

Carboxylated mPEG can also be reacted with hydroxysuccinimide in the presence of dicyclohexylcarbodiimide and dimethyl formamide for reaction with protein:

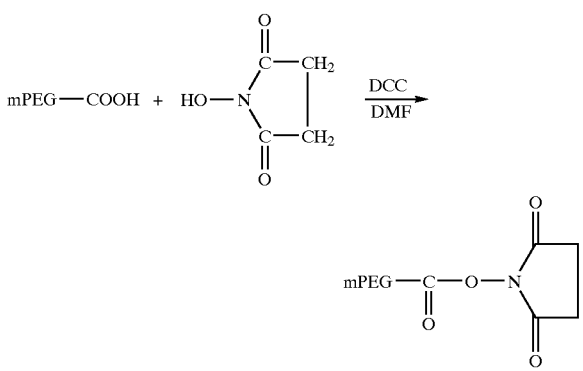

King and Weiner (*Int. J. Peptide Protein Res.* 16:147 (1980) describe the dithiocarbonate of mPEG:

Beauchamp et al., *Analytical Biochem.* 131:25–33 (1983) describe the activation of PEG with 1,1'-carbonyldiimidazole. Reaction of this derivative with a peptide yields a carbamate linkage:

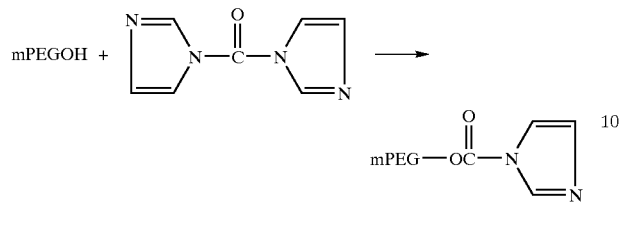

Veronese et al., *Appl. Biochem. & Biotechnol.* 11:141–152 (1985) describe the activation of methoxy poly(ethylene glycol) with phenylchloroformates, e.g., 2,4,5-trichlorophenylchloroformate or p-nitrophenylchloroformate. These derivatives are linked to peptides by urethane linkages:

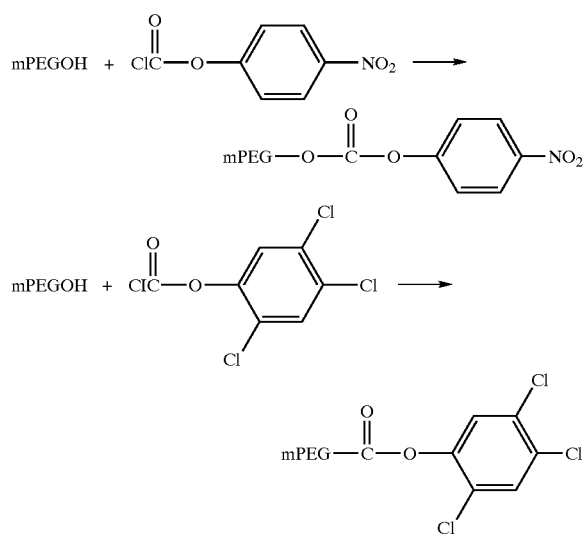

Ueno et al. in European Patent Application 87103259.5 form mPEG imidoesters from the corresponding nitriles by reaction with dry hydrogen chloride in the presence of a dehydrated lower alcohol:

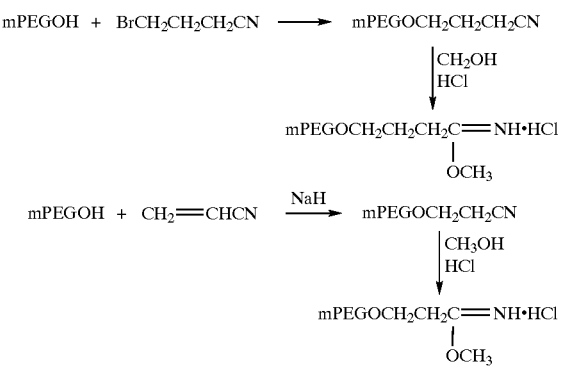

Abuchowski et al., *Cancer Biochem. Biophys.* 7:175–186 (1984) have described forming mPEG succinate as described above and then forming methoxy polyethylene glycolyl succinimidyl succinate ("SS-PEG") by reaction with hydroxysuccinimide in the presence of dicyclohexyl-carbodiimide:

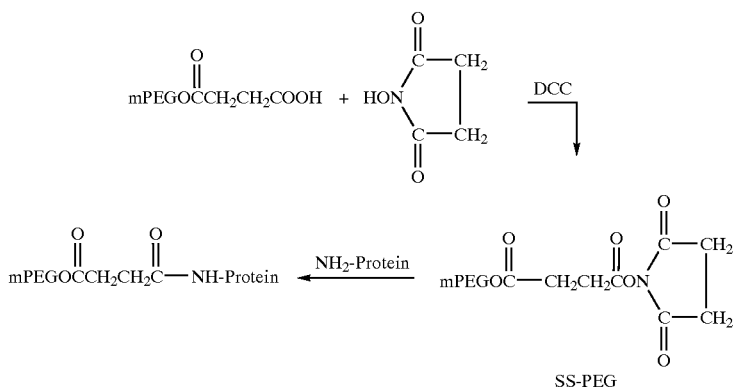

Sano et al., European Patent Application No. 89107960.0 disclose the phenyl glyoxal derivative of methoxy poly(ethylene glycol), which is capable of modifying the guanidino groups in peptides:

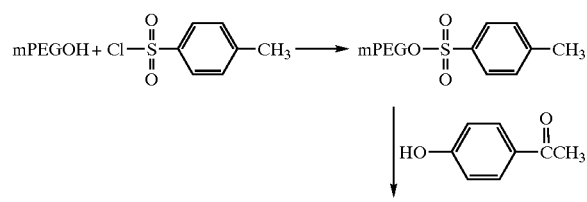

Zalipsky, in U.S. Pat. No. 5,122,614, describes the activation of PEG by conversion into its N-succinimide carbonate derivative ("SC-PEG"):

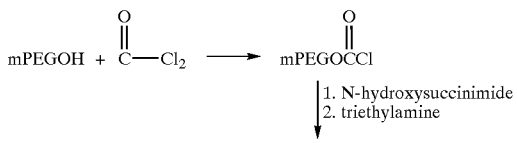

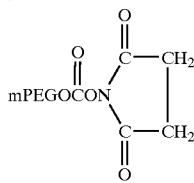

Methoxypoly(ethylene glycol)-succinyl carbonate
SC-PEG

Zalipsky et al., *J. Macromol. Sci. Chem.* A21:839, disclose the amino acid ester derivative of methoxy poly (ethylene glycol):

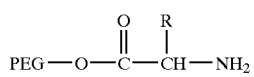

Davis et al., U.S. Pat. No. 4,179,337, disclose a hydrazide derivative of methoxy poly(ethylene glycol), which is capable of modifying aldehydes and ketones and other functional groups:

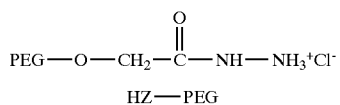

HZ—PEG

It is further disclosed that the bifunctional derivative of PEG, i.e., polyethylene glycol-bis-succinidyl carbonate ("BSC-PEG") can be prepared by similar means. The SC-PEG and BSC-PEG compounds are then reacted with amine groups in a protein and attached thereto via urethane (carbamate) linkages.

It will be readily apparent to those skilled in the art that other activated PAGs can also be employed in the practice of the present invention. The preferred activated PAG for use in the practice of the present invention is selected from the group consisting of SS-PEG and SC-PEG. The use of SC-PEG is most preferred.

Branched Polymers

The invention further provides for the use of branched, substantially non-antigenic polymers for polyalkylene oxide conjugation of the sFv (SCA) proteins corresponding to the formula:

$$(R)_n\text{L-A} \qquad (II)$$

wherein (R) includes a water-soluble non-antigenic polymer;

(n)=2 or 3;
(L) is an aliphatic linking moiety covalently linked to each (R); and
(A) represents an activated functional group capable of undergoing nucleophilic substitution. For example, (A) can be a group which is capable of bonding with biologically active nucleophiles or moieties capable of doing the same.

In particularly preferred aspects of the invention (R) includes a poly(alkylene oxide) PAO such as poly(ethylene glycol) PEG or MPEG. It is preferred that each chain have a molecular weight of between about 200 and about 12,000 daltons and preferably between about 1,000 and about 10,000 daltons. Molecular weights of about 5,000 daltons are most preferred.

As shown in Formula II, 2 or 3 polymer chains, designated (R) herein, are joined to the alphatic linking moiety (L). Suitable aliphatics included substituted alkyl diamines and triamines, lysine esters and malonic ester derivatives. The lining moieties are perferably non-planar, so that the polymer chains are not rigidly fixed. The linking moiety (L) is also a means for attaching the mulitple polymer chains or "branches" to (A), the moeity through which the polymer attaches to the sFv (SCA) protein.

(L) preferably includes a multiply-functionalized alykyl group containing up to 18, and more preferably between 1–10 carbon atoms. A heteroatom such as nitrogen, oxygen or sulfur may be included within the alkyl chain. The alkyl chain may also be branched at a carbon or nitrogen atom. In another aspect of the invention, (L) is a single nitrogen atom.

(L) and (R) are preferably joined by a reaction between nucleophilic functional groups on both (R) and (L). Each (R) is suitably functionalized to undergo nucleophilic substitution and bond with (L). Such functionalization of polymers is readily apparent to those of ordinary skill in the art.

A wide variety of linkages are contemplated between (R) and (L). Urethane (carbamate) linkages are preferred. The bond can be formed, for example, by reacting an amino group such as 1,3-diamino-2-propanol with methoxypolyethylene glycol succinimidyl carbonate as described in U.S. Pat. No. 5,122,614. Amide linkages, which can be formed by reacting an amino-terminated non-antigenic polymer such as methoxypolyethylene glycol-amine (mPEG amine) with an acyl chloride functional group. Examples of other such linkages include ether, amine, urea, and thio and thiol analogs thereof, as well as the thio and thiol analogs of the urethane and amide linkages discussed supra.

The moiety (A) of Formula II represents groups that "activate" the branched polymers of the present invention for conjugation with biologically active materials. (A) can be a moiety selected from:

1. Functional groups capable of reacting with an amino group such as:
   a) carbonates such as the p-nitrophenyl or succinimidyl;
   b) carbonyl imidazole;
   c) azlactones;
   d) cyclic imide thiones; or
   e) isocyanates or isothiocyanates.

2. Functional groups capable of reacting with carboxylic acid groups and reactive with carbonyl groups such as:
   a) primary amines; or
   b) hydrazine and hydrazide functional groups such as the acyl hydrazides, carbazates, semicarbamates, thiocarbazates, etc.

3. Functional groups capable of reacting with mercapto or sulfhydryl groups such as phenyl glyoxals; see, for example, U.S. Pat. No. 5,093,531.

4. Other nucleophiles capable of reacting with an electrophilic center. A non-limiting list includes, for example, hydroxyl, amino, carboxyl, thiol groups, active methylene and the like.

The moiety (A) can also include a spacer moiety located proximal to the aliphatic linking moiety (L). The spacer moiety may be a heteroalkyl, alkoxyl, alkyl containing up to 18 carbon atoms or even an additional polymer chain. The spacer moieties can be added using standard synthesis techniques.

The branched polymers, generally, U-PAO's or U-PEG's, are formed using conventional reaction techniques known to those of ordinary skill in the art.

These umbrella-like branched polymers of the present invention (U-PAO's or U-PEG's) react with biologically active nucleophiles to form conjugates. The point of polymer attachment depends upon the functional group (A). For example, (A) can be a succinimidyl succinate or carbonate and react with ε-amino lysines. The branched polymers can also be activated to link with any primary or secondary amino group, mercapto group, carboxylic acid group, reactive carbonyl group or the like found on biologically active polypeptides. Other groups are apparent to those of ordinary skill in the art.

One of the main advantages of the use of the branched polymers is that the branching imparts an umbrella-like three dimensional protective covering to the materials they are conjugated with. This contrasts with the string-like structure of the straight chain polymers discussed, supra. An additional advantage of the branched ploymers is that they provide the benefits associated with attaching several strands of polymers to a sFv protein but require substantially fewer conjugation sites. The desired properties of PEGylation are realized and the loss of bioactivity is minimized.

One or more of the activated branched polymers can be attached to a biologically active nucleophile, such as an sFv protein, by standard chemical reactions. The conjugate is represented by the formula:

$$[(R)_n L\text{-}A^1]_z\text{-(nucleophile)} \quad \text{(III)}$$

wherein (R) is a water-soluble substantially non-antigenic polymer; n=2 or 3; (L) is an aliphatic linking moiety; ($A^1$) represents a linkage between (L) and the nucleophile and (z) is an integer $\geq 1$ representing the number of polymers conjugated to the biologically active nucleophile. The upper limit for (z) will be determined by the number of available nucleophilic attachment sites and the degree of polymer attachment sought by the artisan. The degree of conjugation can be modified by varying the reaction stoichimetry using well-known techniques. More than one polymer conjugated to the nucleophile can be obtained by reacting a stoichimetric excess of the activated polymer with the nucleophile.

Purification of sFv Proteins

A generic protocol that has been developed and used to produce twelve different single chain antigen binding molecules. It involves cell lysis and washing, solubilization in a denaturing solvent, refolding by dilution, and two ion-exchange HPLC chromatography steps. Such isolated sFvs (SCAs) are capable of being PAG conjugated according to the present invention.

The fermentation of the sFv-producing *E. coli* strains are performed at 32° C. using a casein digest-glucose-salts medium. At an optical density of 18 to 20 at 600 nm, sFv expression is induced by a 42° C. temperature shock for one hour. After the fermentation is cooled to 10° C., the cells are harvested by centrifugation at 7000 g for ten minutes. The wet cell paste is then stored frozen at −20° C. Approximately 200 to 300 g of wet cell paste is normally recovered from one 10-liter fermentation.

For protein recovery, the cell paste from three 10-liter fermentations (600-900 g) is thawed overnight at 4° C. and gently resuspended at 4° C. in 50 mM Tris-HCl, 1.0 mM EDTA, 100 mM KCl, 0.1 mM phenylmethylsulfonyl chloride (PMSF), pH 8.0 (lysis buffer), using 10 liters of lysis buffer for every kilogram of wet cell paste. When thoroughly resuspended, the chilled mixture is passed three times through a Manton-Gaulin cell homogenizer to fully lyse the cells. Because the cell homogenizer raises the temperature of the cell lysate to 25±5° C., the cell lysate is cooled to 5±2° C. with a Lauda/Brinkman chilling coil after each pass. Complete lysis is verified by visual inspection under a microscope.

The cell lysate is centrifuged at 24,300 g for thirty minutes at 6° C. using a Sorvall RC-5B centrifuge. The pellet contains the insoluble sFv and the supernatant is discarded. The pellet is washed by gently scraping it from the centrifuge bottles and resuspending it in 5 liters of lysis buffer/kg of wet cell paste. The resulting 3.0–4.5-liter suspension is again centrifuged at 24,300 g for 30 min at 6° C., and the supernatant is discarded. This washing of the cell pellet removes soluble *E. coli* proteins and can be repeated as many as five times. At any time during this washing procedure the material can be stored as a frozen pellet at −20° C. A substantial time saving in the washing steps can be accomplished by utilizing a Pellicon tangential flow apparatus equipped with 0.22-μm microporous filters.

The washed cell pellet is solubilized at 4° C. in freshly prepared 6 M guanidine hydrochloride, 50 mM Tris-HCl, 10 mM $CaCl_2$, 50 mM KCl, pH 8.0 (denaturing buffer), using 6 ml/g of pellet. If necessary, a few quick pulses from a Heat Systems Ultrasonics tissue homogenizer can be used to complete the solubilization. The resulting suspension is centrifuged at 24,300 g for 45 minutes at 6° C. and the pellet is discarded. The optical density of the supernatant is determined at 280 nm and if the $OD_{280}$ is above 30, additional denaturing buffer is added to obtain an $OD_{280}$ of approximately 25.

The supernatant is slowly diluted into cold (4–7° C.) refolding buffer (50 mM Tris-HCl, 10 mM $CaCl_2$, 50 mM KCl, 0.1 mM PMSF, pH 8.0) until a 1:10 to 1:100 dilution is reached (final volume 70–120 liters). The refolding buffer should be prepared at least one day prior to use, to allow sufficient time for it to cool to 4° C. The best results will be obtained when the supernatant is slowly added to the refolding buffer over a two hour period, with gentle mixing. The solution is left undisturbed for at least twenty hours and then filtered through a Millipore Pellicon tangential flow apparatus at 4° C. with four to six 0.45-μm microporous membranes (HVLP 000 C5). The filtrate is concentrated to 1 to 2 liters using a Pellicon apparatus with four to six 10,000 NMWL cassettes (SK1PA156A4), again at 4° C.

The concentrated crude sFv sample is buffer exchanged at 4° C. into 20 mM 2-[N-morpholino]ethanesulfonic acid (Mes), 0.3 mM $CaCl_2$, pH 6.0, using the Pellicon ultrafiltration apparatus equipped with four to six 10,000 NMWL cassettes. The sample is then chromatographed on a Waters Accell Plus CM ion-exchange (RCM) column (4.7×30.0 cm). Prior to loading on the HPLC, the material is filtered through a 0.22-μm filter and the Accell column is equilibrated with Buffer A (40 mM Mes, 1 mM $CaCl_2$, pH 6.0). Following sample loading, the Accell column is eluted over a 55-minute period with a linear gradient of Buffer A and Buffer B (40 mM Mes, 100 mM $CaCl_2$, pH 7.0). (See Table 1).

TABLE 1

Accell Cation-Exchange HPLC Gradients

| Time (min)[a] | Flow (ml/min) | Buffers[b] | | |
|---|---|---|---|---|
| | | % A | % B | % C |
| Initial | 40.0 | 100 | 0 | 0 |
| 55.0 | 40.0 | 0 | 100 | 0 |
| 58.0 | 40.0 | 0 | 100 | 0 |
| 60.0 | 40.0 | 0 | 0 | 100 |
| 62.0 | 40.0 | 100 | 0 | 0 |

[a]Linear gradients are run between each time point.
[b]Buffer A, 40 mM Mes, 1 mM $CaCl_2$, pH 6.0; Buffer B, 40 mM Mes, 100 mM $CaCl_2$, pH 7.0; Buffer C, 40 mM Mes, 20% ethanol, pH 7.5.

The Accell Plus CM column has a capacity of about 3 g and thus all the crude sFv sample can normally be loaded in a single run. The fractions are analyzed using 4–20% Novex SDS-PAGE gels and the peak fractions are pooled. Normally, the sFv elutes from the Accell ion-exchange column quite early in the gradient. To enhance resolution for certain sFv proteins, holds in the gradient can be implemented.

The pooled fractions from the Accell HPLC purification are dialyzed against Buffer D (40 mM 3-[N-morpholino] propanesulfonic acid (Mops), 0.5 mM Ca acetate, pH 6.0) until the conductivity is lowered to that of Buffer D. The sample is then loaded on a 21.5×150-mm polyaspartic acid PolyCAT A column. If more than 60 mg is loaded on this column, the resolution begins to deteriorate; thus, the pooled fractions from the Accell HPLC purification often must be divided into several PolyCAT A runs. Most sFv proteins have an extinction coefficient of about 2.0 mg ml$^{-1}$ cm$^{-1}$ at 280 nm and this can be used to determine protein concentration. The sFv sample is eluted from the PolyCAT A column with a 50-min linear gradient of Buffer D and Buffer E (40 mM Mops, 10 mM Ca acetate, pH 8.0). See Table 2.

TABLE 2

PolyCAT A Cation-Exchange HPLC Gradients

| Time (min)[a] | Flow (ml/min) | Buffers[b] | | |
|---|---|---|---|---|
| | | % D | % E | % F |
| Initial | 15.0 | 100 | 0 | 0 |
| 50.0 | 15.0 | 0 | 100 | 0 |
| 55.0 | 15.0 | 0 | 100 | 0 |
| 60.0 | 15.0 | 0 | 0 | 100 |
| 63.0 | 15.0 | 0 | 0 | 100 |
| 64.0 | 15.0 | 100 | 0 | 0 |
| 67.0 | 15.0 | 100 | 0 | 0 |

[a]Linear gradients are run between each time point.
[b]Buffer D, 40 mM Mops, 0.5 mM Ca acetate, pH 6.0; Buffer E, 40 mM Mops, 10 mM Ca acetate, pH 8.0; Buffer F, 40 mM Mops, 100 mM CaCl$_2$, pH 7.5.

The sFv proteins will often elute between 20 and 26 min when this gradient is used. This corresponds to an eluting solvent composition of approximately 70% Buffer D and 30% Buffer E.

This purification procedure yields sFv proteins that are more than 95% pure as examined by SDS-PAGE and Scatchard analysis. Modifications of the above procedure may be dictated by the isoelectric point of the particular sFv being purified, which is often between 8.0 and 9.3.

The polyalkylene glycols (PAGs) employed in the practice of the present invention, which, as indicated above, are preferably activated by reaction with a coupler, can be reacted with any of several groups that may be present attached to the chain of the single chain antigen binding molecules, e.g. terminal carboxyl groups, thiol groups, phenolic hydroxyl groups, or primary amino groups located at the chain terminus or along the chain. It is preferred to react activated PAGs with primary amine groups, especially those occurring along the peptide chain. It is most preferred that the activated PAGs be coupled to the E amino groups of lysine residues as well as cysteine residues in the polypeptide.

The reaction between the PAG and the single chain polypeptide is normally carried out in solution, preferably an aqueous buffer solution providing a pH in the range of from about 6 to about 10, preferably from about 7 to about 9, most preferably from about 7 to about 8. As examples of buffer solutions that will provide pH's in these ranges at 25° C. may be listed:

50 ml of 0.1 molar potassium dihydrogen phosphate +5.6 to 46.1 ml 0.1 molar NaOH diluted to 100 ml 50 ml of 0.025 molar borate+2.0 to 20.5 ml 0.1 molar HCl diluted to 100 ml 50 ml of 0.025 molar borate+0.9 to 18.3 ml 0.1 molar NaOH diluted to 100 ml 50 ml of 0.05 molar sodium bicarbonate+5.0 to 10.7 ml 0.1 molar NaOH diluted to 100 ml The precise adjustment of the quantity of acid or base to be used to provide a particular desired pH will be readily determinable by those skilled in the art.

If, in a given instance, the use of a biological buffer should be required, one of the following may be employed:

3-(N-Morpholino)propanesulfonic acid (MOPS)

3-(N-Morpholino)-2-hydroxypropanesufonic acid (MOPSO)

Piperazine-N,N'-bis(2-hydroxypropanesulfonic acid) (POPSO)

The reaction between the PAG and the single chain polypeptide will normally be run under conditions that will not give rise to denaturation, e.g. mild temperatures and no more agitation than necessary. The reaction will preferably be run at a temperature in the range of from about 4° C. to about 25° C. More preferably, the reaction will be run at room temperature, i.e. from about 20° C. to about 25° C.

It will be readily understood by those skilled in the art that the amount of PAG employed relative to the amount of single chain polypeptide will be dependent upon the desired nature of the reaction product. Where, for example, it is desired to react a PAG with each lysine residue along the polypeptide chain, an amount of PAG at least equimolar to the lysine concentration will be required. It will be advantageous to employ an excess of PAG, where possible, in order to increase the reaction rate and the likelihood of a complete reaction. Clearly, if fewer than all of the possible reaction sites along the polypeptide chain are to be derivatized, correspondingly less PAG will be used. In general, however, where molar excesses of PAG's are used, it has been determined that molar excesses on the order of 2–100 of the PAG can be used; molar excesses of 2–10 are preferred.

The time required for the reaction will depend upon a number of factors, such as reaction temperature, concentration of reactants, and whether full or partial reaction is desired. The course of the reaction can be monitored by conventional means, such as the analysis of periodic samples by size exclusion chromatography or gel electrophoresis. The reaction can conveniently be terminated when desired by the addition of a compound having a primary amine group, e.g. glycine, to scavenge the excess PAG. A reaction time of about 15–120 minutes will typically be required to fully react the PAG with the primary amine groups of the lysine residues of the single chain polypeptide at room temperature. The skilled practitioner will understand that the time for conjugation, as well as the amount and type of PAG, must not be such as to inactivate the polypeptide being employed.

Purification of the PAG/single chain polypeptide reaction product can be effected by means commonly employed by those skilled in the art, such as, for example, size exclusion chromatography, ion-exchange chromatography, ultrafiltration, dialysis, and the like. Solutions of the reaction product can, if desired, be concentrated with a rotary evaporator and can be obtained in the dry state by lyophilization.

Depending upon the particular single chain antigen binding molecule chosen and the extent to which it is reacted with the PAG, the resulting adduct is expected to be useful both diagnostically and therapeutically, exhibiting, as compared to the unreacted single chain polypeptide, decreased immunogenicity, increased circulating life, and increased stability while maintaining an acceptable level of activity.

The single chain antigen binding polypeptide can be reacted with the activated branched polyethylene glycol polymers discussed above in an aqueous reaction medium which can be buffered, depending on the pH requirements of the nucleophile. The optimum pH for the reaction is generally between about 6.5 and about 8.0 and preferably about 7.4 for polypeptides. The optimum reaction conditions for the sFv stability, reaction efficiency, etc., is within the level of ordinary skill in the art. The preferred temperature range is between 4° C. and 37° C. The reaction temperature cannot exceed the temperature at which the nucleophile may denature or decompose. It is preferred that the nucleophile be reacted with an excess of the activated branched polymer. Following the reaction, the cojugate is recovered and purified, for example, by diafiltration, column chromatography, combinations thereof, or the like.

Conjugates

Upon production of the polyalkylene oxide conjugated sFv (SCA) of the present invention, the polyalkylene oxide conjugated sFv may further be modified by conjugating a diagnostic or therapeutic agent to the polyalkylene oxide conjugated sFv. The general method of preparing an antibody conjugate according to the invention is described in Shih, L. B., et al., *Cancer Res.* 51:4192 (1991); Shih, L. B., and D. M. Goldenberg, *Cancer Immunol. Immunother.* 31:197 (1990); Shih, L. B., et al., *Intl. J. Cancer* 46:1101 (1990); Shih, L. B., et al., *Intl. J. Cancer* 41:832 (1988), all incorporated herein by reference. The indirect method involves reacting an antibody (or sFv), whose polyalkylene oxide has a functional group, with a carrier polymer loaded with one or plurality of bioactive molecules, such as, peptides, lipids, nucleic acids (i.e., phosphate-lysine complexes), drug, toxin, chelator, boron addend or detectable label molecule(s).

Alternatively, the polyalkylene oxide conjugated sFv may be directly conjugated with a diagnostic or therapeutic agent. The general procedure is analogous to the indirect method of conjugation except that a diagnostic or therapeutic agent is directly attached to an oxidized sFv component. See Hansen et al., U.S. Pat. No. 5,443,953, incorporated herein by reference.

The polyalkylene oxide conjugated sFv can be attached to a derivative of the particular drug, toxin, chelator, boron addend or label to be loaded, in an activated form, preferably a carboxyl-activated derivative, prepared by conventional means, e.g., using dicyclohexylcarbodiimide (DCC) or a water soluble variant thereof, to form an intermediate adduct.

Many drugs and toxins are known which have a cytotoxic effect on tumor cells or microorganisms that may infect a human and cause a lesion, in addition to the specific illustrations given above. They are to be found in compendia of drugs and toxins, such as the Merck Index and the like. Any such drug can be loaded onto a carrier or directly onto a polyalkylene oxide conjugated sFv by conventional means well known in the art, and illustrated by analogy to those described above.

Chelators for radiometals or magnetic resonance enhancers are also well known in the art. Typical are derivatives of ethylenediaminetetraacetic acid (EDTA) and diethylenetriaminepentaacetic acid (DTPA). These typically have groups on the side chain by which the chelator can be attached to a carrier or directly onto a polyalkylene oxide conjugated sFv. Such groups include, e.g., a benzylisothiocyanate, by which the DTPA or EDTA can be coupled to the reactive group of an sFv.

Labels such as radioisotopes, enzymes, fluorescent compounds, electron transfer agents, and the like can also be linked to carrier or directly onto a polyalkylene oxide conjugated sFv by conventional methods well known to the art. These labels and the sFv conjugates prepared from them can be used for immunoassays and for immunohistology, much as the sFv conjugate prepared by direct attachment of the labels to the sFv. However, the loading of the conjugates according to the present invention with a plurality of labels can increase the sensitivity of assays or histological procedures, where only low extent of binding of the sFv to target antigen is achieved.

Boron addends, e.g., carboranes, when attached to single-chain antigen binding molecules and targeted to lesions, can be activated by thermal neutron irradiation and converted to radioactive atoms which decay by alpha emission to produce highly cytotoxic short-range effects. High loading of boron addends, as well as of magnetic resonance enhancing ions, is of great importance in potentiating their effects. Carboranes can be made with carboxyl functions on pendant side chains, as is well known in the art.

Loading of drugs on the carrier will depend upon the potency of the drug, the efficiency of sFv targeting and the efficacy of the conjugate once it reaches its target. In most cases, it is desirable to load at least 20, preferably 50, and often 100 or more molecules of a drug on a carrier. The ability to partially, or completely detoxify a drug as a conjugate according to the invention, while it is in circulation, can reduce systemic side effects of the drug and permit its use when systemic administration of the unconjugated drug would be unacceptable. Administration of more molecules of the drug, but conjugated to the sFv on a carrier, according to the present invention, permits therapy while mitigating systemic toxicity.

Toxins will often be less heavily loaded than drugs, but it will still be advantageous to load at least 5, preferably 10 and in some cases 20 or more molecules of toxin on a carrier and load at least one carrier chain on the sFv for targeted delivery.

Uses

The polyalkylene oxide conjugated sFv (SCA) polypeptide conjugates of the present invention are expected to have much longer circulating half lifes and reduced immunogenicity in vivo. This may solve a potential limitation relating to very rapid blood clearance of some sFv proteins. It would also reduce or eliminate concerns about repeated administration of a therapeutic sFv which may otherwise provoke an immune response in the patient. The choice of the particular cysteine and/or oligo-lysine mutant combinations may allow one to achieve circulating lives over a considerable range depending on the specific polyalkylene oxide conjugated sFv variant polypeptide. This would allow sFv to be administered for the therapeutic use of choice.

A diagnostic or therapeutic agent is a molecule or atom which is conjugated to an antibody and useful for diagnosis or for therapy. The immunoreactivity of the antibody is retained. Diagnostic or therapeutic agents include drugs, toxins, chelators, boron compounds and detectable labels. See "Conjugates" section, supra, for further details.

The diagnostic or therapeutic agent may be, but is not limited to, at least one selected from a nucleic acid, a compound, a protein, an element, a lipid, an antibody, a saccharide, an isotope, a carbohydrate, an imaging agent, a lipoprotein, a glycoprotein, an enzyme, a detectable probe, or any combination thereof, which may be detectably labeled as for labeling antibodies, as described herein. Such labels include, but are not limited to, enzymatic labels, radioisotope or radioactive compounds or elements, fluorescent compounds or metals, chemiluminescent compounds and bioluminescent compounds. Alternatively, any other known diagnostic or therapeutic agent can be used in a method of the present invention.

A therapeutic agent used in the present invention may have a therapeutic effect on the target cell, the effect selected from, but not limited to, correcting a defective gene or protein, a drug action, a toxic effect, a growth stimulating effect, a growth inhibiting effect, a metabolic effect, a catabolic affect, an anabolic effect, an antiviral effect, an antibacterial effect, a hormonal effect, a neurohumoral effect, a cell differentiation stimulatory effect, a cell differentiation inhibitory effect, a neuromodulatory effect, an antineoplastic effect, an anti-tumor effect, an insulin stimulating or inhibiting effect, a bone marrow stimulating effect, a pluripotent stem cell stimulating effect, an immune system stimulating effect, and any other known therapeutic effects that may be provided by a therapeutic agent delivered to a cell via a delivery system according to the present invention.

The sFv conjugate of the present invention may be used for protection, suppression or treatment of infection or disease. By the term "protection" from infection or disease as used herein is intended "prevention," "suppression" or "treatment." "Prevention" involves administration of a glycosylated sFv conjugate prior to the induction of the disease. "Suppression" involves administration of the composition prior to the clinical appearance of the disease.

"Treatment" involves administration of the protective composition after the appearance of the disease. It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis."

Such additional therapeutic agents which can further comprise a therapeutic agent or composition of the present invention may be selected from, but are not limited to, known and new compounds and compositions including antibiotics, steroids, cytotoxic agents, vasoactive drugs, antibodies and other therapeutic modalities. Non-limiting examples of such agents include antibiotics used in the treatment of bacterial shock, such as gentamycin, tobramycin, nafcillin, parenteral cephalosporins, etc; adrenal corticosteroids and analogs thereof, such as methyl prednisolone, mitigate the cellular injury caused by endotoxins; vasoactive drugs, such as alpha receptor blocking agent (e.g., phenoxybenzamine), beta receptor agonists (e.g., isoproterenol), and dopamine are agents suitable for treating septic shock.

Polyalkylene oxide conjugated sFv of the invention may also be used for diagnosis of disease and to monitor therapeutic response. Other uses of polyalkylene oxide conjugated sFv proteins are specific targeting of pro-drug activating enzymes to tumor cells by a bispecific molecule with specificity for tumor cells and enzyme. Polyalkylene oxide conjugated sFv may be used for specific delivery of drug to an in vivo target, such as a tumor, delivery of radioactive metals for tumor radioimmunodiagnosis or radioimmunotherapy (Goldenberg, D. M., *Am. J. Med.* 94:297 (1993)), nonradioactive metals in applications such as with boron/uranium-neutron capture therapy (Ranadive, G. N., et al., *Nucl. Med. Biol.* 20:1 (1993); Barth, R. F., et al., *Bioconjug. Chem.* 5:58 (1994)), and nuclear magnetic resonance imaging (Sieving, P. F., et al., *Bioconjug. Chem.* 1:65 (1990)). This list is illustrative only.

The invention also extends to uses for the polyalkylene oxide conjugated sFv proteins in purification and biosensors. Affinity purification is made possible by affixing the polyalkylene oxide conjugated sFv protein to a support, with the antigen-binding sites exposed to and in contact with the ligand molecule to be separated, and thus purified. Biosensors generate a detectable signal upon binding of a specific antigen to an antigen-binding molecule, with subsequent processing of the signal. Polyalkylene oxide conjugated sFv proteins, when used as the antigen-binding molecule in biosensors, may change conformation upon binding, thus generating a signal that may be detected.

The invention is also directed to a method of detecting an antigen suspected of being in a sample by contacting the sample with the polyalkylene oxide conjugated sFv that is labeled. A sample may comprise at least one compound, mixture, surface, solution, emulsion, suspension, mixture, cell culture, fermentation culture, cell, tissue, secretion and/or derivative or extract thereof.

Such samples can also include, e.g., animal tissues, such as blood, lymph, cerebrospinal fluid (CNS), bone marrow, gastrointestinal contents, and portions, cells or internal and external secretions of skin, heart, lung and respiratory system, liver, spleen, kidney, pancreas, gall bladder, gastrointestinal tract, smooth, skeletal or cardiac muscle, circulatory system, reproductive organs, auditory system, the autonomic and central nervous system, and extracts or cell cultures thereof. Such samples can be measured using methods of the present invention in vitro, in vivo and in situ.

Such samples can also include environmental samples such as earth, air or water samples, as well as industrial or commercial samples such as compounds, mixtures, surfaces, aqueous chemical solutions, emulsions, suspensions or mixtures.

Additionally, samples that can be used in methods of the present invention include cell culture and fermentation media used for growth of prokaryotic or eukaryotic cells and/or tissues, such as bacteria, yeast, mammalian cells, plant cells and insect cells.

Essentially all of the uses for which monoclonal or polyclonal antibodies, or fragments thereof, have been envisioned by the prior art, can be addressed by the polyalkylene oxide conjugated sFv proteins of the present invention. These uses include detectably-labeled forms of the polyalkylene oxide conjugated sFv protein. Types of labels are well-known to those of ordinary skill in the art. They include radiolabeling, chemiluminescent labeling, fluorochromic labeling, and chromophoric labeling. Other uses include imaging the internal structure of an animal (including a human) by administering an effective amount of a labeled form of the polyalkylene oxide conjugated sFv protein and measuring detectable radiation associated with the animal. They also include improved immunoassays, including sandwich immunoassay, competitive immunoassay, and other immunoassays wherein the labeled antibody can be replaced by the PEGylated sFv protein of this invention. See, e.g., Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, pp. 563–681, Elsevier, N (1981); Sambrook et al., *Molecular Cloning—A Laboratory Manual*, 2nd ed., Cold Spring Harbor Laboratory (1989).

Administration

Administration of polyalkylene oxide conjugated sFv conjugates of the invention for in vivo diagnostic and therapeutic applications will be by analogous methods to sFv where the diagnostic or therapeutic principle is directly linked to the sFv or a loaded carrier is linked by random binding to amine or carboxyl groups on amino acid residues of the sFv in a non-site-specific manner.

Conjugates of the present invention (immunoconjugates) can be formulated according to known methods to prepare pharmaceutically useful compositions, such as by admixture with a pharmaceutically acceptable carrier vehicle. Suitable vehicles and their formulation are described, for example, in *Remington's Pharmaceutical Sciences,* 18th ed., Osol, A., ed., Mack, Easton Pa. (1990). In order to form a pharmaceutically acceptable composition suitable for effective administration, such compositions will contain a therapeutically effective amount of the immunoconjugate, either alone, or with a suitable amount of carrier vehicle.

Additional pharmaceutical methods may be employed to control the duration of action. Controlled release preparations may be achieved by the use of polymers to complex or absorb the immunoconjugate of the present invention. The controlled delivery may be exercised by selecting appropriate macromolecules (for example, polyesters, polyamino acids, polyvinyl pyrrolidone, ethylene-vinylacetate, methylcellulose, carboxymethylcellulose, or protamine sulfate). The rate of drug release may also be controlled by altering the concentration of such macromolecules. Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the immunoconjugate of the invention in microcapsules prepared, for example, by coacervation techniques or by interfacial polymerization, for example, by the use of hydroxymethylcellulose or gelatin-microcapsules or poly (methylmethacrylate) microcapsules, respectively, or in a colloid drug delivery system, for example, liposomes, albumin microspheres, microemulsions, nanoparticles, nanocapsules, or in macroemulsions. Such teachings are disclosed in *Remington's Pharmaceutical Sciences,* 16th ed., Osol, A., ed., Mack, Easton Pa. (1990).

The immunoconjugate may be provided to a patient by means well known in the art. Such means of introduction include oral means, intranasal means, subcutaneous means, intramuscular means, intravenous means, intra-arterial means, or parenteral means. Intravenous, intraarterial or intrapleural administration is normally used for lung, breast, and leukemic tumors. Intraperitoneal administration is advised for ovarian tumors. Intrathecal administration is advised for brain tumors and leukemia. Subcutaneous administration is advised for Hodgkin's disease, lymphoma and breast carcinoma. Catheter perfusion is useful for metastatic lung, breast or germ cell carcinomas of the liver. Intralesional administration is useful for lung and breast lesions.

For therapeutic or diagnostic applications, compositions according to the invention may be administered parenterally in combination with conventional injectable liquid carriers such as sterile pyrogen-free water, sterile peroxide-free ethyl oleate, dehydrated alcohol, or propylene glycol. Conventional pharmaceutical adjuvants for injection solution such as stabilizing agent, solubilizing agents and buffers, such as ethanol, complex forming agents such as ethylene diamine tetraacetic acid, tartrate and citrate buffers, and high-molecular weight polymers such as polyethylene oxide for viscosity regulation may be added. Such compositions may be injected intramuscularly, intraperitoneally, or intravenously.

Further non-limiting examples of carriers and diluents include albumin and/or other plasma protein components such as low density lipoproteins, high density lipoproteins and the lipids with which these serum proteins are associated. These lipids include phosphatidyl choline, phosphatidyl serine, phosphatidyl ethanolamine and neutral lipids such as triglycerides. Lipid carriers also include, without limitation, tocopherol.

At least one polyalkylene oxide conjugated sFv linked to a therapeutic agent according to the invention may be administered by any means that achieve their intended purpose, for example, to treat various pathologies, such as cell inflammatory, allergy, tissue damage or other related pathologies.

A typical regimen for preventing, suppressing, or treating various pathologies comprises administration of an effective amount of an sFv conjugate, administered over a period of one or several days, up to and including between one week and about 24 months.

It is understood that the dosage of the present invention administered in vivo or in vitro will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the most preferred dosage will be tailored to the individual subject, as is understood and determinable by one of skill in the art, without undue experimentation. See, e.g., Berkow et al., eds., *Merck Manual,* 16th edition, Merck and Co., Rahway, N.J. (1992); Goodman et al., eds., *Goodman and Gilman's The Pharmacological Basis of Therapeutics,* 8th edition, Pergamon Press, Inc., Elmsford, N.Y. (1990); *Avery's Drug Treatment: Principles and Practice of Clinical Pharmacology and Therapeutics,* 3rd edition, ADIS Press, LTD., Williams and Wilkins, Baltimore, Md. (1987), Ebadi, *Pharmacology,* Little, Brown and Co., Boston (1985), Katzung, *Basic and Clinical Phamacology,* Appleton and Lange, Norwalk, Conn. (1992), which references and references cited therein, are entirely incorporated herein by reference.

The total dose required for each treatment may be administered by multiple doses or in a single dose. Effective amounts of a diagnostic/pharmaceutical compound or composition of the present invention are from about 0.001 µg to about 100 mg/kg body weight, administered at intervals of 4–72 hours, for a period of 2 hours to 5 years, or any range or value therein, such as 0.01–1.0, 1.0–10, 10–50 and 50–100 mg/kg, at intervals of 1–4, 6–12, 12–24 and 24–72 hours, for a period of 0.5, 1.0–2.0, 2.0–4.0 and 4.0–7.0 days, or 1, 1–2, 2–4, 4–52 or more weeks, or 1, 2, 3–10, 10–20, 20–60 or more years, or any range or value therein.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods. See, e.g., Berker, supra, Goodman, supra, Avery, supra and Ebadi, supra, which are entirely incorporated herein by reference, including all references cited therein.

Pharmaceutical compositions comprising at least one type of sFv conjugate of the invention, or, 1, 2, 3, 4, 5, 6, 7, 8, 9 or 10 types of sFv conjugates, of the present invention may be contained in an amount effective to achieve its intended purpose. In addition to at least one sFv conjugate, a pharmaceutical composition may contain suitable pharmaceutically acceptable carriers, such as excipients, carriers and/or auxiliaries which facilitate processing of the active compounds into preparations which can be used pharmaceutically.

Pharmaceutical compositions may also include suitable solutions for administration intravenously, subcutaneously, dermally, orally, mucosally or rectally, and contain from about 0.01 to 99 percent, preferably from about 20 to 75 percent of active component (i.e., the sFv) together with the excipient. Pharmaceutical compositions for oral administration include tablets and capsules. Compositions which can be administered rectally include suppositories. See, e.g., Berker, supra, Goodman, supra, Avery, supra and Ebadi, supra. Additional lipid and lipoprotein drug delivery systems that may be included herein are described more fully in *Annals N.Y. Acad. Sci.* 507:775–88, 98–103, and 252–271, which disclosure is hereby incorporated by reference.

The compositions may also be formulated into orally administrable compositions containing one or more physiologically compatible carriers or excipients, and may be solid or liquid in form. These compositions may, if desired, contain conventional ingredients such as binding agents, for example, syrups, acacia, gelatin, sorbitol, tragacanth, or polyvinylpyrrolidone; fillers, such as lactose, mannitol, starch, calcium phosphate, sorbitol, cyclodextran, or methylcellulose; lubricants such as magnesium stearate, high molecular weight polymers such as polyethylene glycols, high molecular weight fatty acids such as stearic acid or silica; disintegrants such as starch; acceptable wetting agents as, for example, sodium lauryl sulfate.

The oral compositions may assume any convenient form, such as tablets, capsules, lozenges, aqueous or oily suspensions, emulsions, or dry products suitable for reconstitution with water or other liquid medium prior to use. The liquid oral forms may, of course, contain flavors, sweeteners, preservatives such as methyl or propyl p-hydroxybenzoates; suspending agents such as sorbitol, glucose or other sugar syrup, methyl, hydroxymethyl, or carboxymethyl celluloses or gelatin; emulsifying agents such as lecithin or sorbitan monooleate or thickening agents. Non-aqueous compositions may also be formulated which comprise edible oils as, for example, fish-liver or vegetable oils. These liquid compositions may conveniently be encapsulated in, for example, gelatin capsules in a unit dosage amount.

The pharmaceutical compositions according to the present invention may also be administered, if appropriate, either topically as an aerosol or, formulated with conventional bases as a cream or ointment.

The pharmaceutical compositions of the present invention can also be administered by incorporating the active ingredient into colloidal carriers, such as liposomes. Liposome technology is well known in the art, having been described by Allison et al., *Nature* 252:252–254 (1974), and Dancy et al., *J. Immunol.* 120:1109–1113 (1978).

Having now generally described this invention, the same will be better understood by reference to certain specific examples, which are included for the purpose of illustration and not intended to be limiting unless otherwise specified.

EXAMPLES

Example 1

Preparation of Methoxypoly(ethylene glycol)-succinimidyl Carbonate (SC-PEG)

Dissolve 60 g of methoxy poly(ethylene glycol) (MW 5,000) in 200 ml of 3/1 toluene/dichloromethane and treat with a toluene solution of phosgene (30 ml, 57 mmol) overnight. Evaporate the solution to dryness and remove the remainder of the phosgene under vacuum. Redissolve the residue in 150 ml of 2/1 toluene/dichloromethane. Treat the resulting solution with 2.1 g (18 mmol) of solid N-hydroxysuccinimide, followed by 1.7 ml (12 mmol) of triethylamine. Allow the solution to stand for three hours and then filter it and evaporate it to dryness. Dissolve the residue in 600 ml of warm (50° C.) ethyl acetate, filter the solution, and cool it to facilitate precipitation of the polymer. Collect the product by filtration, then recrystallize from ethyl acetate, and dry under vacuum over $P_2O_5$.

Example 2

Preparation of CC 49/212 SCA

In the production of monovalent or multivalent antigen-binding proteins, the same recombinant *E. coli* production system that was used for prior single-chain antigen-binding protein production was used. See Bird et al., *Science* 242:423 (1988). This production system produced between 2 and 20% of the total *E. coli* protein as single-chain antigen-binding protein. For protein recovery, the frozen cell paste from three 10-liter fermentations (600–900 g) was thawed overnight at 4° C. and gently resuspended at 4° C. in 50 mM Tris-HCl, 1.0 mM EDTA, 100 mM KCl, 0.1 mM PMSF, pH 8.0 (lysis buffer), using 10 liters of lysis buffer for every kilogram of wet cell paste. When thoroughly resuspended, the chilled mixture was passed three times through a Manton-Gaulin cell homogenizer to totally lyse the cells. Because the cell homogenizer raised the temperature of the cell lysate to 25±5° C., the cell lysate was cooled to 5±2° C. with a Lauda/Brinkman chilling coil after each pass. Complete lysis was verified by visual inspection under a microscope.

The cell lysate was centrifuged at 24,300 g for 30 minutes at 6° C. using a Sorvall RC-5B centrifuge. The pellet containing the insoluble single-chain antigen-binding protein was retained, and the supernatant was discarded. The pellet was washed by gently scraping it from the centrifuge bottles and resuspending it in 5 liters of lysis buffer/kg of wet cell paste. The resulting 3.0-to 4.5-liter suspension was again centrifuged at 24,300 g for 30 minutes at 6° C., and the supernatant was discarded. This washing of the pellet removes soluble *E. coli* proteins and can be repeated as many as five times. At any time during this washing procedure the material can be stored as a frozen pellet at −20° C. A substantial time saving in the washing steps can be accomplished by utilizing a Pellicon tangential flow apparatus equipped with 0.22-µm microporous filters, in place of centrifugation.

The washed pellet was solubilized at 4° C. in freshly prepared 6 M guanidine hydrochloride, 50 mM Tris-HCl, 10 mM $CaCl_2$, 50 mM KCl, pH 8.0 (dissociating buffer), using 9 ml/g of pellet. If necessary, a few quick pulses from a Heat Systems Ultrasonics tissue homogenizer can be used to complete the solubilization. The resulting suspension was centrifuged at 24,300 g for 45 minutes at 6° C. and the pellet was discarded. The optical density of the supernatant was determined at 280 nm and if the $OD_{280}$ was above 30, additional dissociating buffer was added to obtain an $OD_{280}$ of approximately 25.

The supernatant was slowly diluted into cold (4–7° C.) refolding buffer (50 mM Tris-HCl, 10 mM $CaCl_2$, 50 mM KCl, pH 8.0) until a 1:10 dilution was reached (final volume 10–20 liters). Re-folding occurs over approximately eighteen hours under these conditions. The best results are obtained when the GuHCl extract is slowly added to the refolding buffer over a two hour period, with gentle mixing. The solution was filtered through a 0.2 µm Millipore Millipak 200. This filtration step may be optionally preceded by a centrifugation step. The filtrate was concentrated to 1 to 2 liters using an Amicon spiral cartridge with 10,000 MWCO cartridge, again at 4° C.

The concentrated crude antigen-binding protein sample was dialyzed against Buffer G (60 mM MOPS, 0.5 mM Ca acetate, pH 6.0–6.4) until the conductivity was lowered to that of Buffer G. The sample was then loaded on a 21.5× 250-mm polyaspartic acid PolyCAT A column, manufactured by Poly LC of Columbia, Md. If more than 60 mg of protein is loaded on this column, the resolution begins to deteriorate; thus, the concentrated crude sample often must be divided into several PolyCAT A runs. Most antigen-binding proteins have an extinction coefficient of about 2.0 ml mg$^{-1}$cm$^{-1}$ at 280 nm and this can be used to determine protein concentration. The antigen-binding protein sample was eluted from the PolyCAT A column with a 50-min linear gradient from Buffer G to Buffer H (60 mM MOPS, 20 mM Ca Acetate, pH 7.5–8.0). Most of the single-chain proteins elute between 20 and 26 minutes when this gradient is used. This corresponds to an eluting solvent composition of approximately 70% Buffer G and 30% Buffer H. Most of the bivalent antigen-binding proteins elute later than 45 minutes, which correspond to over 90% Buffer H.

Example 3

Modification of CC 49/212 Single Chain Antigen Binding Molecule with SC-PEG

A sample of CC 49/212 single chain antigen binding molecule (MW=27000) dissolved in KPO$_4$/NaCl buffer (pH 7.2) was obtained as described in Example 2. The protein was found to be pure using SDS-PAGE (sodium dodecyl sulfate-polyacrylamide gel electrophoresis) and size exclusion chromatography. The concentration of the protein was 0.79 mg/ml. It was further concentrated to at least 2 mg/ml using an Amicon concentrator with a 10,000 dalton nominal size cut-off, i.e., anything greater than 10K is retained.

The modification reaction, i.e., the coupling of the SC-PEG to the CC 49/212, was carried out in 50 mM KPO$_4$, 150 mM NaCl buffer, which was the storage buffer the protein was supplied in. The pH was raised from 7.2 to 7.5. SC-PEG (MW 5,000) was added in a 50× molar excess to protein. At specific time intervals, the coupling reaction was terminated by the addition of a 50× molar excess of glycine and the extent and progress of the coupling reaction was checked as a function of time using both size exclusion chromatography using a DuPont Zorbax 250 column and SDS-PAGE.

Free SC-PEG remaining in the samples was removed by extensive dialysis on an Amicon Centricon 10.

The samples were checked for degree of modification by size exclusion chromatography. After concentrating the samples, the residual amine concentration on the protein was determined by titration with trinitrobenzene sulfonate and the percentage of amine groups that had reacted with the SC-PEG (the "% modification") was calculated from the results.

Dansyl derivatives of native single chain antigen binding molecule (CC 49/212) and hemoglobin, PEG SCA and hemoglobin, and N-acetyl lysine were prepared. These samples were then analyzed for amino acid. The results of this experiment are shown in Table 3.

TABLE 3

| Reaction Time (Minutes) | Protein (mg/ml) | % Modification | Molecular Weight[1] (Kilodaltons) |
|---|---|---|---|
| 0 | 0.74148 | 0 | 27 |
| 15 | 1.3569 | 52 | 84 |
| 30 | 1.3587 | 62 | 156 |
| 60 | 1.2706 | 63 | |
| 80 | | | 224 |
| 90 | | | 247 |
| 120 | 0.78 | 65 | |

[1]Molecular weights were determined by size exclusion chromatography after calibration against standards.

Example 4

Competition ELISA

The CC49 monoclonal antibody was developed by Dr. Jeffrey Schlom's group, Laboratory of Tumor Immunology and Biology, National Cancer Institute. It binds specifically to the pan-carcinoma tumor antigen TAG-72. See Muraro, R. et al., Cancer Research 48: 4588–4596 (1988).

FIG. 1 is a graphical representation of three competition ELISA's in which unlabeled PEG modified CC49/212 single-chain Fv (closed squares), CC49/212 single-chain Fv (open squares), CC49 IgG (open circles), and MOPC-21 IgG (+) competed against a CC49 IgG radiolabeled with $^{125}$I for binding to the TAG-72 antigen on a human breast melanoma extract. MOPC-21 is a control antibody that does not bind to TAG-72 antigen. In this experiment, 50% competition of $^{125}$I-CC49 IgG binding required about 200 nM of CC49 IgG, about 550 nM of CC49/212 sFv, and about 3000 nM of PEG modified CC49/212 sFv.

Example 5

Preparation of U-PEG-OH

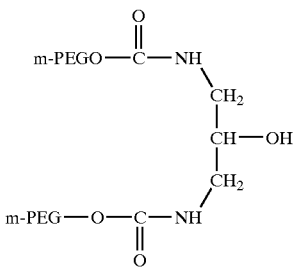

Materials

Methoxypoly(ethylene glycol) (m-PEG) was obtained from Union Carbide. The solvents were obtained from Aldrich Chemical of Milwaukee, Wis. The methoxypoly (ethylene glycol)-N-succinimidyl carbonate (SC-PEG) was prepared as described in U.S. Pat. No. 5,122,614, using m-PEG having a molecular weight of about 5,000. Each of the products prepared in Examples 5–10 was confirmed structurally by carbon-13 NMR.

The branched polymer, U-PEG-OH, was prepared by adding 100 mg (1.1 mmol) of 1,3-diamino-2-propanol to a solution of 10.0 g (2 mmol) of SC-PEG in 50 mL of methylene chloride. The mixture was stirred for 18 hours at room temperature then filtered. Excess solvent was removed by distillation in vacuo. The residue was recrystallized from 2-propanol to yield 7.1 g of product (70% yield).

Example 6

Preparation of U-PNP-PEG

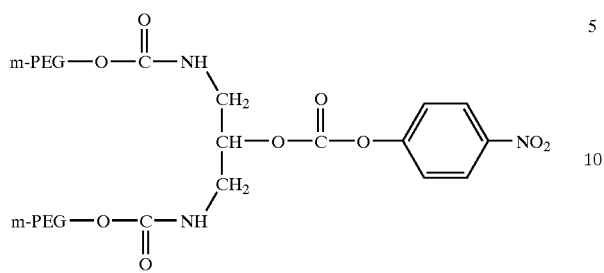

The compound of Example 5 was activated with p-nitrophenyl chloroformate. First, 5.0 g (0.5 mmol) of U-PEG-OH was azeotropically dried by refluxing in 75 mL of toluene for 2 hours, resulting in the removal of 25 mL of solvent/water. The reaction mixture was cooled to 30° C., followed by the addition of 120 mg (0.6 mmol) of p-nitrophenyl chloroformate and 50 mg (0.6 mmol) of pyridine. The resulting mixture was stirred for two hours at 45° C., followed by stirring overnight at room temperature.

The reaction mixture was then filtered through CELITE™, followed by removal of the solvent from the filtrate by distillation in vacuo. The residue was recrystallized from 2-propanol to yield 4.2 g (81% yield) of the product.

Example 7

Preparation of US-PEG

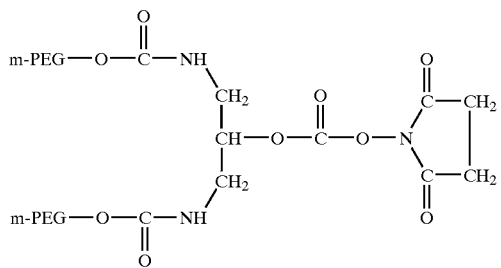

In this example, the U-PNP-PEG of Example 6 was reacted with N-hydroxysuccinimide to form the succinimidyl carbonate ester of U-PEG. A solution containing 5.0 g (0.5 mmol) of the U-PNP-PEG, 0.6 g (5 mmol) of N-hydroxysuccinimide and 0.13 g (1 mmol) of diisopropylethylamine in 40 ml of methylene chloride was refluxed for 18 hours. The solvent was then removed by distillation in vacuo, and the residue was recrystallized from 2-propanol to yield 4.2 g of the succinimidyl carbonate ester (82% yield).

Example 8

Preparation of XU-PEG-OH

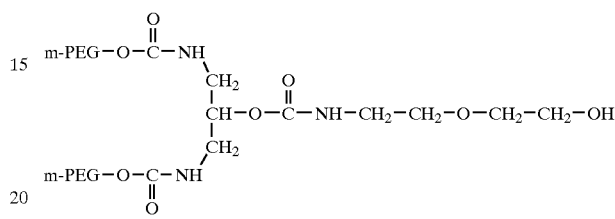

This branched polymer was prepared by reacting the U-PNP-PEG of Example 6 with 2-(2-aminoethoxy) ethanol (i.e., the amino alcohol was reacted with the p-nitrophenyl carbonate). The recrystallized product yield was 86%.

Example 9

Preparation of XU-PNP-PEG

The compound of Example 8 was functionalized with p-nitrophenyl carbonate as in Example 6. The recrystallized product yield was 83%.

Example 10

Preparation of XUS-PEG

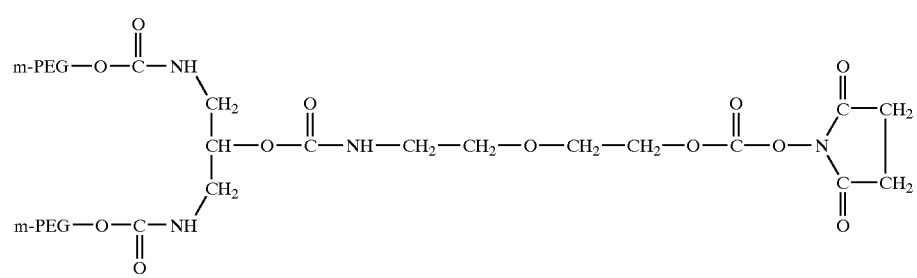

In this example, the succinimidyl carbonate derivative of compound prepared in Example 8 was prepared according to the process described in Example 7, by reacting N-hydroxysuccinimide with the p-nitrophenyl carbonate derivative of Example 9. The recovered product yield was 84%.

Example 11

Modification of CC49/218 with SC-PEG or XUS-PEG

A sample containing CC49/218 was desalted on a PD-10 column in a buffer consisting of 0.1M sodium phosphate, pH 8.0. An equimolar amount of SC-PEG or XUS-PEG was added and the reactions were incubated at 4° C., overnight. The reactions were quenched with an excess of glycine. The modified CC49/218 conjugates were GPC purified and then concentrated in a centricon-10.

The yield based on GPC integration was about 50% for SC-PEG modified CC49/218 and about 40% for XUS-PEG modified CC49/218. The GPC profiles were almost identical to those obtained when the reaction was performed at pH9.0, room temperature. SDS-PAGE revealed that the appropriate derivatives had been made.

Example 12

Competition ELISA

Figure 4:
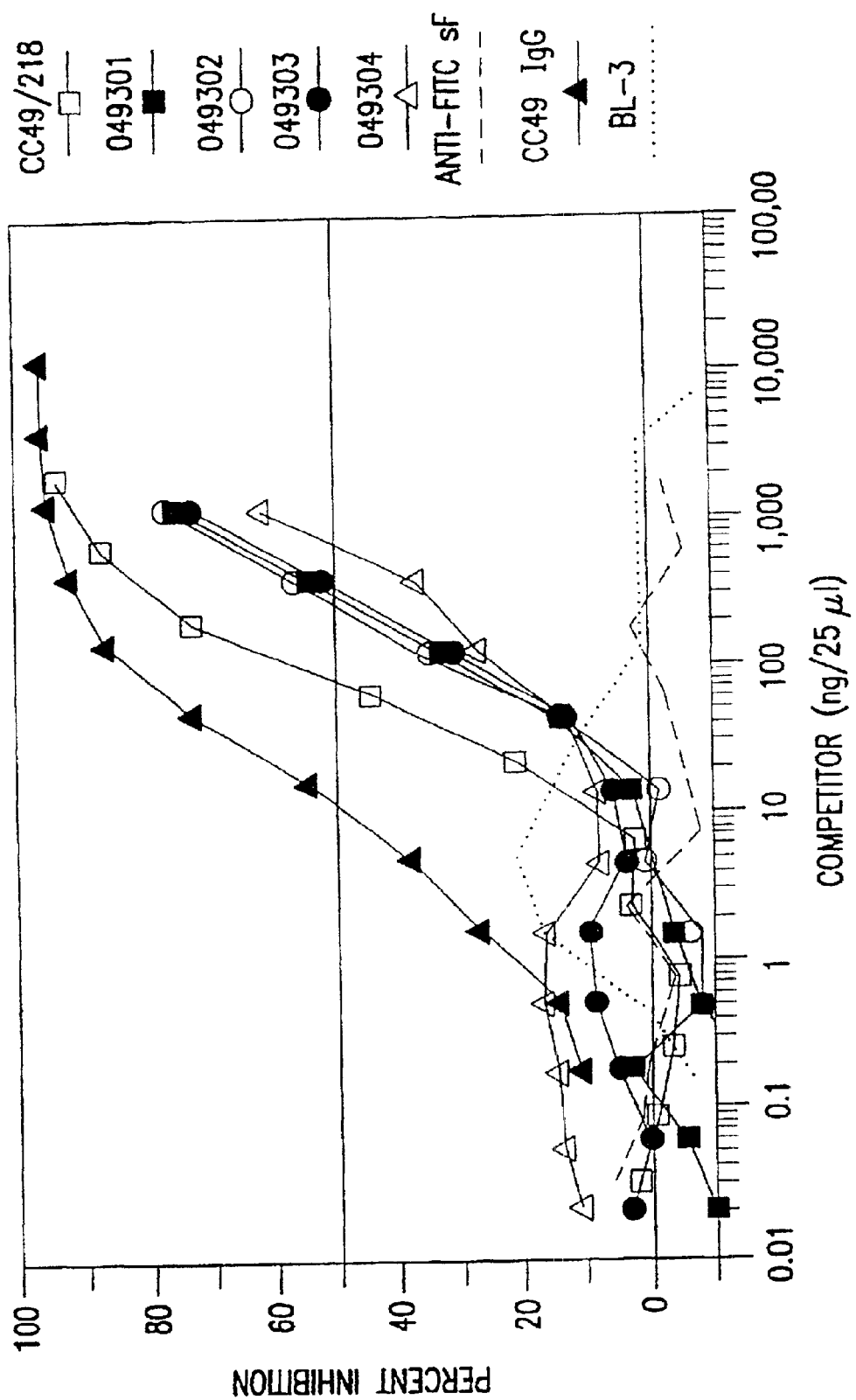
FIG. 4 is a graphical representation of three competition ELISA's in which unlabeled SC-PEG unreacted CC49/218 SCA (closed squares), CC49/218 SCA (open squares), unlabeled XUS-PEG unreacted CC49/218 SCA (open circles), SC-PEG modified CC49/218 SCA (closed circles), XUS-PEG modified CC49/218 SCA (open triangles), CC49 IgG (closed triangles), an Anti-FITC SCA (dashed line) or BL-3 IgG (dotted line) were competed against a CC49 IgG radiolabeled with $^{125}$I for binding to the TAG-72 antigen on a human breast carcinoma extract.

The assay was performed as in Example 4 above using SC-PEG modified CC49/218 and XUS-PEG modified CC49/218 along with the appropriate controls. The results are shown in FIG. 4 and in Table 4 below.

| Sample | 50% Inhibition (nM) |
|---|---|
| CC49 IgG | 10 |
| GC49/218 sFv | 80 |
| SC Unreacted #049301 | 300 |
| SC Reacted #049304 | 650 |
| XUS Unreacted #049302 | 280 |
| XUS Reacted #049303 | 320 |

Thus, the affinity of the SC-PEG modified CC49-SCA was within about 8 to 10 fold of the native CC49-SCA and the affinity the XUS-PEG modified CC49-SCA was within about 4 to 5 fold of the native CC49-SCA.

Samples #049304 and #049303 were PEG modified, whiles samples #04901 and #049302 were unmodified CC49/218 isolated from the reaction mixtures.

Example 13

Pharmacokinetics of Plasma Retention of sFv and PEG-sFv

Figure 5:
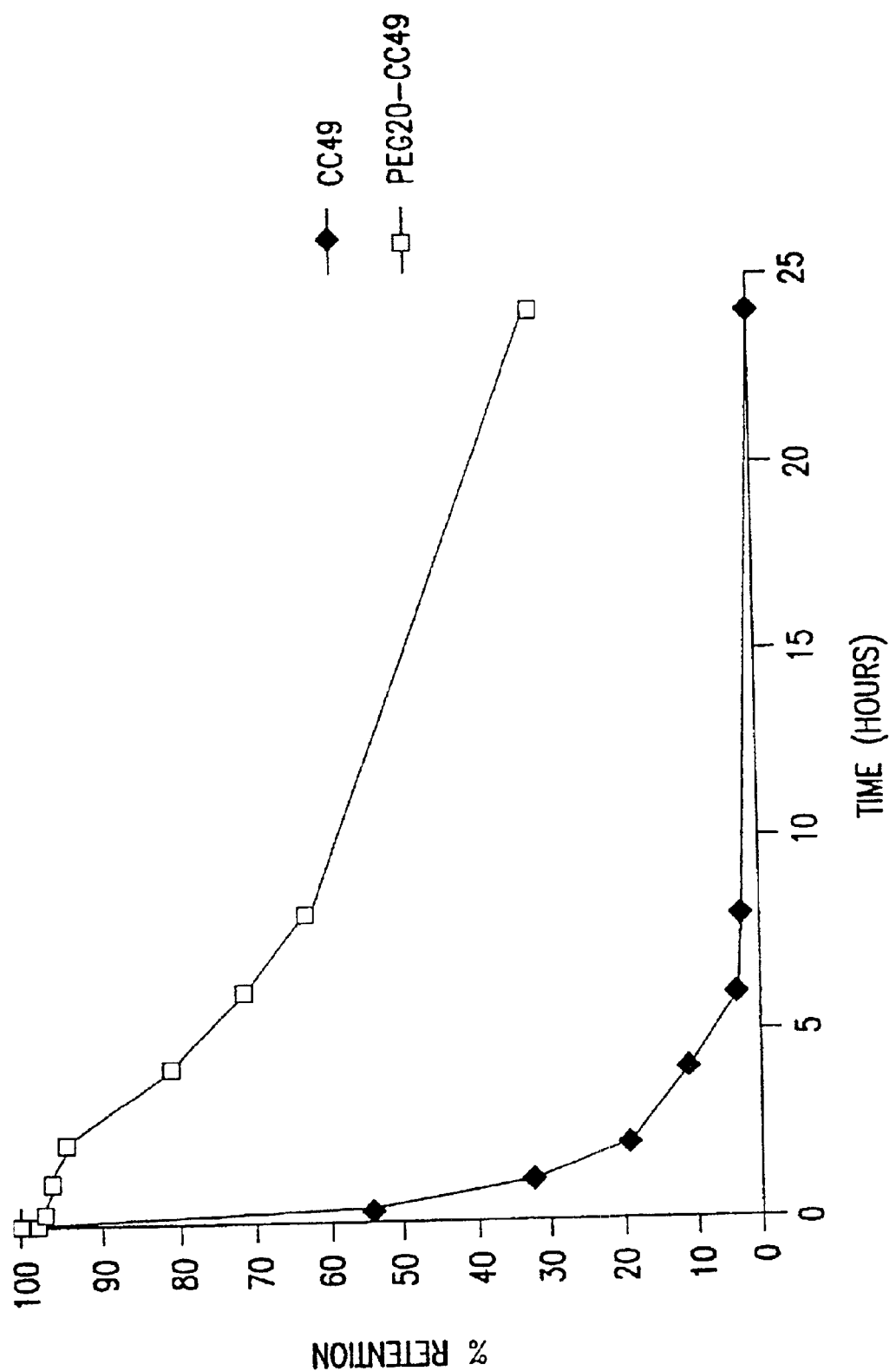
FIG. 5 shows the pharmacokinetics of plasma retention of SCA and PEG-SCA. The details of the experiment are described in Example 13.

Sixty μg of CC49/218 sFv protein or 60 μg of PEG-modified sFv protein were injected intravenously at time 0 into ICR (CD-1) female mice (Harlan—25 g, 7–8 weeks old). Mice were bled at the time points indicated in FIG. 5. The percent retention in plasma was quantitated by ELISA methods. For the PEG-modified conjugate, CC49/218 sFv was conjugated to SC-PEG of molecular mass 20,000 (the protocol is described in U.S. Pat. No. 5,122,614, which disclosure is incorporated herein by reference). The average PEG:sFv molar ratio in the tested PEG-sFv conjugate was approximately 1:1.

Example 14

PEGylated Multimer Single Chain Antibodies

Using bifunctional PEG, dimers and trimers of CC49-SCA have been made. CC49-SCA was modified with bifunctional PEG as follows: 2 ml of CC49-SCA in phosphate buffered saline (25 mM sodium phosphate, pH 7.3, 0.15 M NaCl) at a concentration of 1.5 mg/ml was modified as follows. Bifunctional PEG (polyethylene glycol with reactive SC at both terminal ends), 1.887 mg (powder) was dissolved in 0.1 ml of MOPS (3-[N-morpholino]propane)-sulfonic acid) buffered at pH 7.3. This PEG solution was added to CC49-SCA solution within 10 seconds of dissolution. The mixture was then stirred at 24° C. for 1 hour. At the end of the reaction, solid Guanidine HCl was added to the reaction mixture to a final concentration of 6 M in order to break up non covalently associated CC49-SCA. This material was immediately applied to a size exclusion column (2 cm×60 cm, Superdex-75) previously equilibrated in the buffer composed of 60 mM Guanidine HCl in 50 mM Tris pH 7.3, 1 mM $CaCl_2$, 0.1 mM PMSF (phenyl methyl sulfonyl flouride), and 50 mM KCl. Multimers of different molecular weights were then fractionated from the column.

These multimers are CC49-SCA separated by a long stretch of PEG (5000 MW, about 226 carbons in length) and were freshly refolded and thus, are not believed to arise from aggregation. It is less likely that there was diabody or multivalent SCA formed as a result of self association of the CC49-SCA. Further evidence was demonstrated by the fact that there was negligible native CC49-SCA in the denaturing SDS-PAGE profile.

Figure 6:
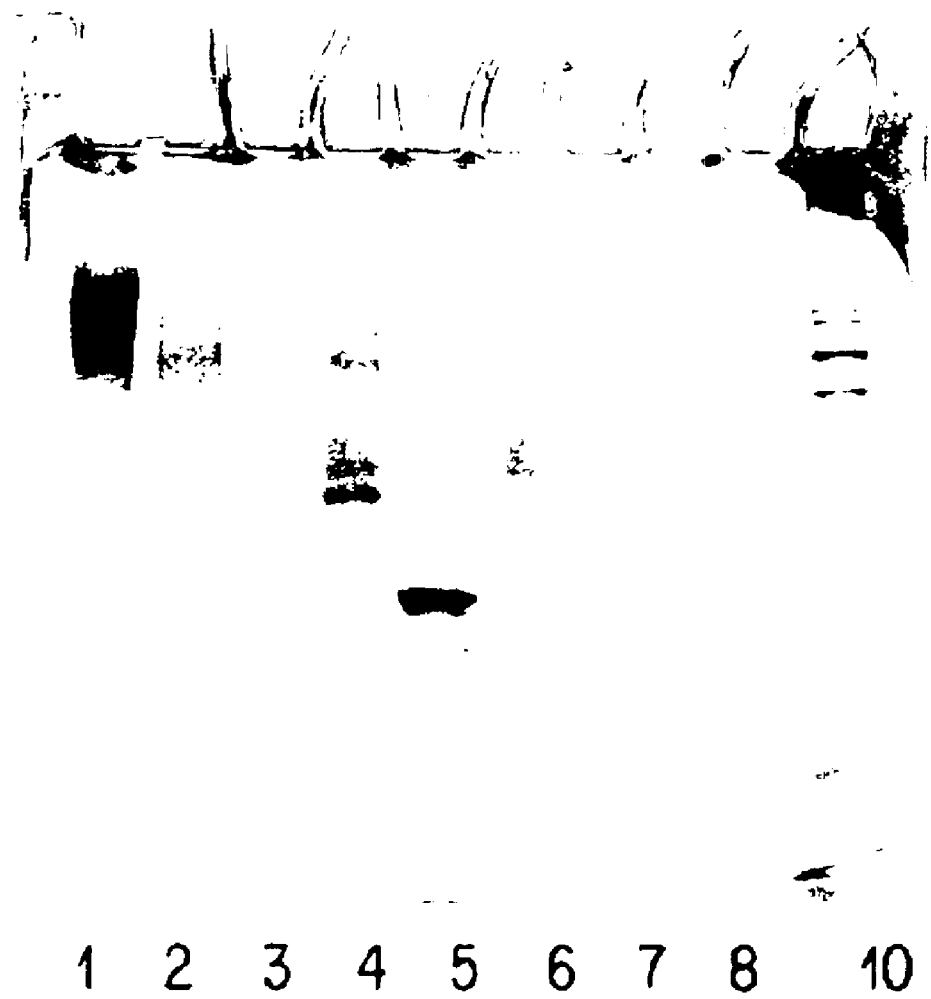
FIG. 6 shows an SDS-PAGE of the purified CC49-multimers cross-linked by PEG5000 under reducing conditions. The details of the experiment are described in Example 14. The lanes of the gel contain the following: 1) trimeric form; 2) dimeric form; 3) dimeric form; 4) mixed population; 5) native CC49; 6) PEG-CC49 monomer; 7) PEG-CC49 monomer; 8) empty; 9) empty; and 10) molecular weight standards.

The SDS-PAGE electrophoresis patterns for dimeric CC49-SCA, trimeric CC49-SCA, PEG-CC49-SCA and native CC49-SCA under reducing conditions are shown in FIG. 6.

The multimers were assayed for binding affinity using the following assay which was modified method described in B Friquet et al. *J. of Immunology Methods,* 77:305–319(1985). Briefly, various amounts of a given modified single chain antibody were mixed with various amounts of the antigen mucin in PBS (phosphate buffered saline). The binding reaction was allowed to reach equilibration for at least 24 hours at 4° C. At the end of the incubation, the unbound CC49-SCA fractions were assayed by ELISA, while the bound fractions were washed away. The total amount of free CC49-SCA was determined by the ELISA using the CC49-SCA sample pre-incubated in the absence of the antigen mucin. The bound antibody was determined by subtraction of the free (unbound) amount from the total amount as determined by ELISA. Since the total amount of the CC49-SCA was known, it was also used as its own standard curve. Note that each type of CC49-SCA had its own reference control. In essence, the protocol was measuring the unbound amount of a particular version of PEG-CC49-SCA as a result of the binding to the antigen. Although PEG may affect the detection reagent in ELISA, this was well contained in the standard references. Therefore, the amount measured was not due to the difference of various PEG on the various versions of PEG-CC49-SCA.

Figure 7:
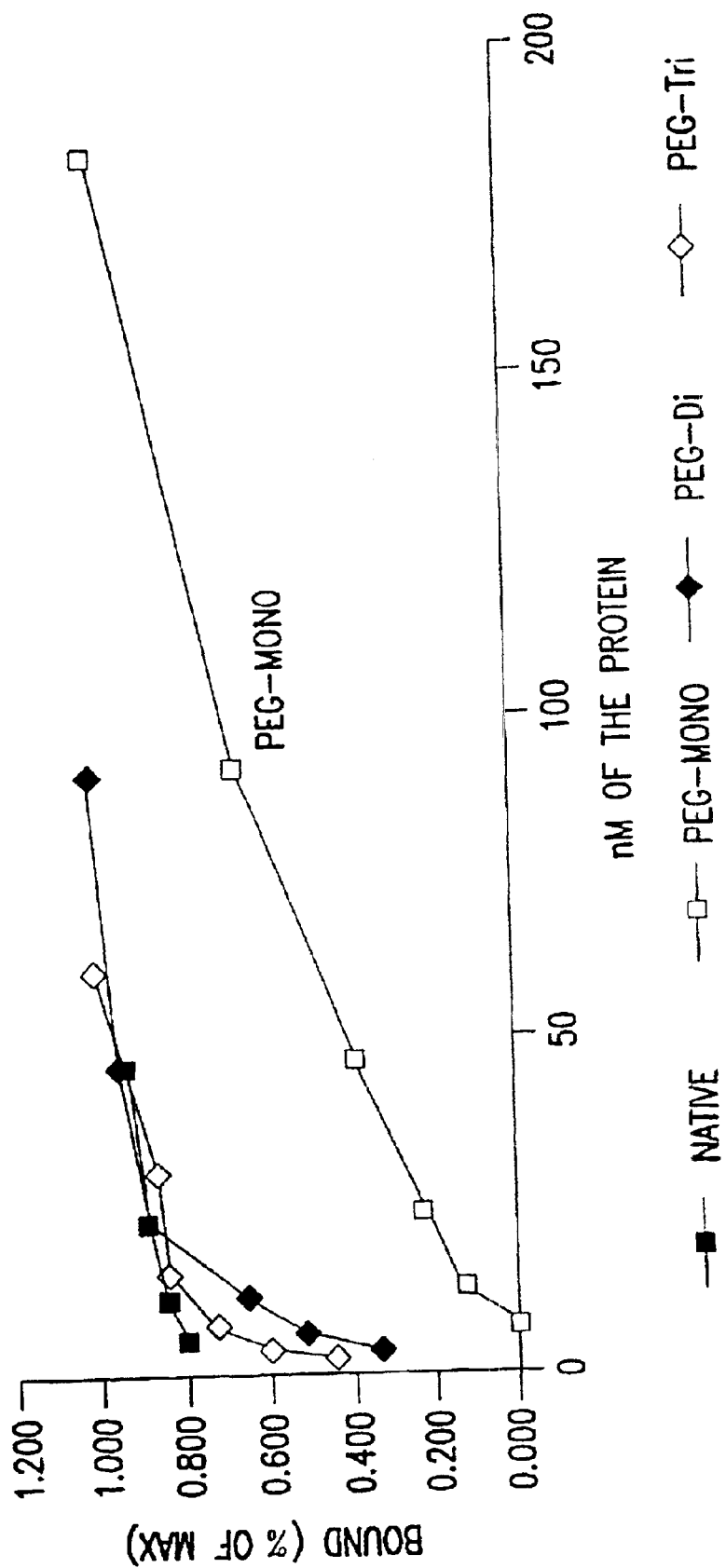
FIG. 7 shows the binding kinetics of Mono-, Di-, Tri-, -PEG-CC49. The details of the experiment are described in Example 14. Native CC49 is represented by the solid box. PEG-mono-CC49 is represented by the open box. PEG-Di-CC49 is represented by the solid diamond. PEG-Tri-CC49 is represented by the open diamond.

In sum, in this study, increasing concentrations of the CC49-SCA protein were allowed to bind to a fixed amount of the antigen. The amount that binds to 50% of the maximal level is a good indication of the affinity. This data indicate that the affinity of PEG-Di-CC49-SCA and PEG-Tri-CC49-SCA are very similar to that of native CC49-SCA. However, the PEG-modified CC49-SCA monomer had much lower affinity. The binding data are shown in FIG. 7.

Example 15

Pharmacokinetics of PEG-CC49-SCA

The pharmacokinetic study of various forms of PEG-CC49-SCA was performed as in Example 13, above.

The data obtained from this study indicate the following:

There was a trend toward longer circulation half-lives as the size of the PEG increases. As more PEG is attached to the protein, the circulation time increases. However, attachment of a few strands of high molecular weight PEG gives a better increase in circulation half-life than multiple stands of lower molecular weight PEG.

The circulation half-life of CC49-SCA-U-PEG, made with the US-PEG prepared in Example 7, was about the same as that of CC49-SCA-PEG-12000. Therefore, the shape of the PEG does not affect the circulation half-life.

Whether the linker is an SC-bond, Flan-bond, hydrazine bond, or TPC, there was no significant change in the circulation half-life. Therefore, the chemical bonds of the linkers, if not releasable, do not affect the circulation half-life. In addition, the PEG remains attached to the protein during the observable time.

The circulation half-life was shortened by carbohydrate. However, if PEG was attached to the carbohydrate, it increases the circulation by about 10 fold. This was not better, however, than attaching an equivalent number of PEG at other sites on CC49-SCA.

The results of the study are shown in the table below:

Example 16

Competition Binding Assay

A competition binding assay of biotinylated CC49-SCA with various PEGylated CC49-SCA proteins was performed using an ELISA of the biotinylated CC49-SCA as detected by horseradish-peroxidase conjugated with streptoavidin (SAV-HRP). In the assay, the biotinylated CC49-SCA and PEG-CC49-SCA sample were mixed at various ratios for competition of binding to the antigen mucin on a surface. The amount of biotinylated-CC49-SCA bound to antigen was then measured by SAV-HRP, which would not detect the PEG-modified CC49-SCA. The reduction of binding of biotinylated CC49-SCA due to competition of PEG-CC49-SCA is a reflection of the relative affinity of the two forms of CC49-SCA for the antigen. The level of PEG-CC49-SCA that caused reduction of biotin-CC49-SCA to half of its maximum binding level (IC50) was used in the Cheng-Prussoff formula for determination of the affinity constant Kd as follows: Assuming the biotin-CC49-SCA level is [s] and its affinity is known as Ks, then the affinity for the PEG-CC49-SCA is $Kd=IC50/(1+[s]/Ks)$. Note that PEG-CC49-SCA was not directly measured and that PEG had no effect on biotin binding because it was on a different molecule. The estimated Kd was then expressed as a percentage of the control (CC49-SCA).

The affinity ranking obtained was as follows:

CC49=SC2>GC=Bio.CC49=CC12>C20=F5>HZ>PG where SC2 is PEG SC2000-CC49-SCA; GC is glyco-CC49-SCA; Bio.CC49-SCA is the biotinylated CC49-SCA; CC12 is the PEG-SC12,000-CC49-SCA; F5 is PEG-Flan-5000-

Pharmacokinetic Data of SCA and PEG-SCA

| Native CC49 or PEG used | | | # PEG per SCA | Circulatory half-life (hours) | | Area Under the Curve ($\mu$g/ml-hour) | | Mean Residence Time (hours) | |
| --- | --- | --- | --- | --- | --- | --- | --- | --- | --- |
| MW | Linker | Label | | Mean | Std. Error | Mean | Std. Error | Mean | Std. Error |
| Native CC49/218 | | | 0 | 0.69 | 0.41 | 54 | 27 | 1 | 0.59 |
| 2,000 | SC | | 2.1 | 3.41 | 0.38 | 135.91 | 13.02 | 4.92 | 0.55 |
| 3,400 | NHS | biotin | 2 | 2.52 | 0.45 | 95.03 | 14.48 | 3.64 | 0.65 |
| 5,000 | Flan | | 1 | 1.81 | 0.44 | 67.41 | 13.98 | 2.61 | 0.63 |
| 5,000 | SC | | 1.7 | 4.15 | 1.08 | 147.96 | 32.7 | 5.98 | 1.56 |
| 5,000 | TPC | | 1.4 | 3.48 | 0.95 | 120.56 | 28.05 | 5.02 | 1.37 |
| 5,000 | Hz | | 4.8 | 9.81 | 1.61 | 395.33 | 56.32 | 14.15 | 2.32 |
| 10,000 | U | biotin | 1.5 | 10.42 | 1.36 | 415.86 | 47.21 | 15.03 | 1.96 |
| 12,000 | Flan | | 1.2 | 13.98 | 1.76 | 583.19 | 64.47 | 20.17 | 2.53 |
| 12,000 | SC | | 1.3 | 13.27 | 1.5 | 586.05 | 58.08 | 19.15 | 2.16 |
| 20,000 | SC | | 1 | 12.86 | 0.73 | 1,111 | 56 | 18.55 | 1.05 |
| Native gCC49/3 | | | 0 | 0.39 | 0.01 | 36 | 1 | 0.56 | 0.02 |
| 5,000 | Hz | | 4.2 | 3.84 | 0.46 | 305 | 31 | 5.54 | 0.66 |

NOTES:
A. The PK modeling was following a one-compartment, i.v.-bolus model.
B. The observed vs. predicted correlations are over 95%.
C. The circulatory half-life is the time for the drug concentration in the serum to reduce to one half after equilibration is reached (about 2 min.)
D. AUC = area under the curve, is the integral of the drug blood level over time from zero to last measurement, and is a measure of quantity of drug absorbed and in the body.
E. Mean residence time is the average amount of time a drug remains in the compartment.
F. The code for linkers are:
SC = Succinimidyl Carbonate
Hz = Hydrazide
Flan = Thiazolidine thione ester
NHS = N-hydroxy succinimide
TPC = trichlorophenyl carbonate
U = SC in the middle of PEG
The Flan-bond PEG was prepared as taught in U.S. Pat. No. 5,405,877.

Figure 8:
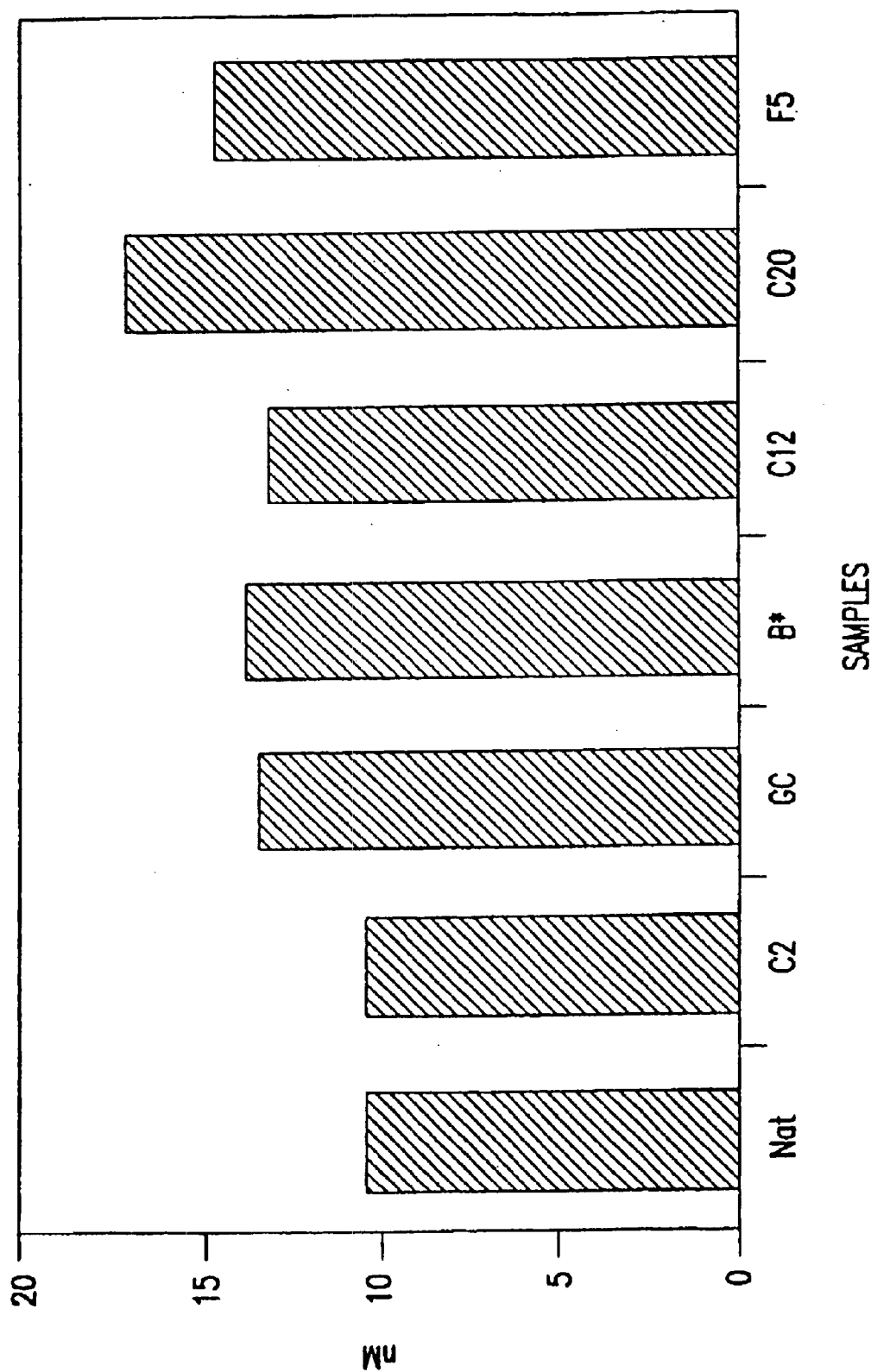
FIG. 8 shows the results of the competition assay performed in Example 16. Nat is native CC49-SCA, C2 is PEG SC2000-CC49-SCA; GC is glyco-CC49-SCA; B* is the biotinylated CC49-SCA; C12 is the PEG-SC12,000-CC49-SCA; F5 is PEG-Flan-5000-CC49-SCA; and C20 is PEG-SC20000-CC49-SCA.

CC49-SCA; HZ is CC49-SCA highly PEGylated on the carboxyl groups with MW 5000 hydrazine-PEG; PG is PEG-glyco-CC49-SCA and is highly PEGylated on the carbohydrate with MW 5000 hydrazine PEG; and C20 is PEG-SC20000-CC49-SCA. The affinity for all the PEG-modified CC49-SCAs shown in FIG. 8, were within about two fold of the native CC49-SCA. Taken together with the data in Example 15 (see, the table), the results indicate that when the SCA is modified with a lower number of PEG molecules, the resulting affinity of the SCA is better than when the SCA is modified with a higher number of PEG molecules.

Although the foregoing refers to particular preferred embodiments, it will be understood that the present invention is not so limited. It will occur to those skilled in the art that various modifications may be made to the disclosed embodiments and that such modifications are intended to be within the scope of the present invention.

What is claimed is:

1. A single-chain antigen-binding polypeptide capable of site specific polyalkylene oxide conjugation that comprises,
    (a) a first polypeptide comprising an antigen-binding portion of a variable region of an antibody heavy or light chain;
    (b) a second polypeptide comprising an antigen-binding portion of a variable region of an antibody heavy or light chain; and
    (c) a peptide linker linking the first and second polypeptides, wherein the single-chain antigen-binding polypeptide has at least three consecutive Lys residues that are capable of polyalkylene oxide conjugation, and wherein any one of said consecutive Lys residues is located at a position selected from the group consisting of
    (i) any amino acid position of the peptide linker;
    (ii) an amino acid position adjacent to the C-terminus of the first or the second polypeptide; and
    (iii) combinations thereof, wherein the polyalkylene oxide conjugated single-chain antigen-binding polypeptide is capable of binding an antigen; and
    wherein the single-chain antigen-binding polypeptide is monovalent or multivalent.

2. The single-chain antigen-binding polypeptide of claim 1, wherein said Lys residue capable of polyalkylene oxide conjugation is located at an amino acid position adjacent to the C-terminus of the second polypeptide.

3. The single-chain antigen-binding protein of claim 1, that is bivalent or trivalent, and that is encoded as a single, multivalent protein.

4. The single-chain antigen-binding polypeptide of claim 1, wherein said first polypeptide comprises the antigen-binding portion of the variable region of an antibody light chain and the second polypeptide comprises the antigen-binding portion of the variable region of an antibody heavy chain.

5. The single-chain antigen-binding polypeptide of claim 1, wherein the C-terminus of the second polypeptide is native to the second polypeptide.

6. The single-chain antigen-binding polypeptide of claim 5, wherein the C-terminus of the second polypeptide further comprises an addition of one or a plurality of amino acid residue(s), such that the polyalkylene oxide conjugated single-chain antigen-binding polypeptide is capable of binding an antigen.

7. The single-chain antigen-binding polypeptide of claim 1 that is illustrated by FIGS. 3A–3B.

8. The single-chain antigen-binding polypeptide of claim 1 wherein the peptide linker ranges from 10 to 30 amino acid residues in length.

9. The single-chain antigen-binding polypeptide of claim 1 wherein the peptide linker is less than 15 amino acid residues in length.

10. The single-chain antigen-binding polypeptide of claim 1 wherein any one of said consecutive Lys residues is located at amino acid position 77 of the light chain variable region.

11. The single-chain antigen-binding polypeptide of claim 1 wherein anyone of said consecutive Lys residues is located at any amino acid position of the peptide linker.

12. The single-chain antigen-binding polypeptide of claim 1 wherein any one of said consecutive Lys residues is located at an amino acid position selected from the group consisting of positions 82B, and 82C of the heavy chain variable region.

13. The single-chain antigen-binding polypeptide of claim 5 wherein any one of said consecutive Lys residues is located at an amino acid position adjacent to the C-terminus of the second polypeptide.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 749 base pairs
      (B) TYPE: nucleic acid
      (C) STRANDEDNESS: double
      (D) TOPOLOGY: both (ii) MOLECULE TYPE: cDNA (ix) FEATURE:
      (A) NAME/KEY: CDS
      (B) LOCATION: 1..738

(xi) SEQUENCE DESCRIPTION: SEQ ID NO: 1:

```
GAC GTC GTG ATG TCA CAG TCT CCA TCC TCC CTA CCT GTG TCA GTT GGC        48
Asp Val Val Met Ser Gln Ser Pro Ser Ser Leu Pro Val Ser Val Gly
 1               5                  10                  15

GAG AAG GTT ACT TTG AGC TGC AAG TCC AGT CAG AGC CTT TTA TAT AGT        96
Glu Lys Val Thr Leu Ser Cys Lys Ser Ser Gln Ser Leu Leu Tyr Ser
                20                  25                  30

GGT AAT CAA AAG AAC TAC TTG GCC TGG TAC CAG CAG AAA CCA GGG CAG       144
Gly Asn Gln Lys Asn Tyr Leu Ala Trp Tyr Gln Gln Lys Pro Gly Gln
            35                  40                  45

TCT CCT AAA CTG CTG ATT TAC TGG GCA TCC GCT AGG GAA TCT GGG GTC       192
Ser Pro Lys Leu Leu Ile Tyr Trp Ala Ser Ala Arg Glu Ser Gly Val
        50                  55                  60

CCT GAT CGC TTC ACA GGC AGT GGA TCT GGG ACA GAT TTC ACT CTC TCC       240
Pro Asp Arg Phe Thr Gly Ser Gly Ser Gly Thr Asp Phe Thr Leu Ser
 65                 70                  75                  80

ATC AGC TGT GTG AAG ACT GAA GAC CTG GCA GTT TAT TAC TGT CAG CAG       288
Ile Ser Cys Val Lys Thr Glu Asp Leu Ala Val Tyr Tyr Cys Gln Gln
                85                  90                  95

TAT TAT AGC TAT CCC CTC ACG TTC GGT GCT GGG ACC AAG CTT GTG CTG       336
Tyr Tyr Ser Tyr Pro Leu Thr Phe Gly Ala Gly Thr Lys Leu Val Leu
               100                 105                 110

AAA GGC TCT TGT TCC GGT AGC GGC AAA CCC GGG AGT GGT GAA GGT AGC       384
Lys Gly Ser Cys Ser Gly Ser Gly Lys Pro Gly Ser Gly Glu Gly Ser
           115                 120                 125

ACT AAA GGT CAG GTT CAG CTG CAG CAG TCT GAC GCT GAG TTG GTG AAA       432
Thr Lys Gly Gln Val Gln Leu Gln Gln Ser Asp Ala Glu Leu Val Lys
       130                 135                 140

CCT GGG GCT TCA GTG AAG ATT TCC TGC AAG GCT TCT GGC TAC ACC TTC       480
Pro Gly Ala Ser Val Lys Ile Ser Cys Lys Ala Ser Gly Tyr Thr Phe
145                 150                 155                 160

ACT GAC CAT GCA ATT CAC TGG GTG AAA CAG AAC CCT GAA CAG GGC CTG       528
Thr Asp His Ala Ile His Trp Val Lys Gln Asn Pro Glu Gln Gly Leu
               165                 170                 175
```

```
GAA TGG ATT GGA TAT TTT TCT CCC GGA AAT GAT GAT TTT AAA TAC AAT      576
Glu Trp Ile Gly Tyr Phe Ser Pro Gly Asn Asp Asp Phe Lys Tyr Asn
        180                 185                 190

GAG AGG TTC AAG GGC AAG GCC ACA CTG ACT GCA GAC AAA TCC TCC AGC      624
Glu Arg Phe Lys Gly Lys Ala Thr Leu Thr Ala Asp Lys Ser Ser Ser
            195                 200                 205

ACT GCC TAC GTG CAG CTC AAC TGC CTG ACA TCT GAG GAT TCT GCA GTG      672
Thr Ala Tyr Val Gln Leu Asn Cys Leu Thr Ser Glu Asp Ser Ala Val
        210                 215                 220

TAT TTC TGT ACA AGA TCC CTG AAT ATG GCC TAC TGG GGT CAA GGA ACC      720
Tyr Phe Cys Thr Arg Ser Leu Asn Met Ala Tyr Trp Gly Gln Gly Thr
225                 230                 235                 240

TCA GTC ACC GTC TCC TGC TAATAGGATC C                                 749
Ser Val Thr Val Ser Cys
                245

(2) INFORMATION FOR SEQ ID NO: 2:

(i) SEQUENCE CHARACTERISTICS:
        (A) LENGTH: 246 amino acids
        (B) TYPE: amino acid
        (D) TOPOLOGY: linear (ii) MOLECULE TYPE: protein (xi) SEQUENCE DESCRIPTION: SEQ ID NO: 2:

Asp Val Val Met Ser Gln Ser Pro Ser Ser Leu Pro Val Ser Val Gly
 1               5                  10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Cys Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Gly Ser Cys Ser Gly Ser Gly Lys Pro Gly Ser Gly Glu Gly Ser
        115                 120                 125

Thr Lys Gly Gln Val Gln Leu Gln Gln Ser Asp Ala Glu Leu Val Lys
    130                 135                 140

Pro Gly Ala Ser Val Lys Ile Ser Cys Lys Ala Ser Gly Tyr Thr Phe
145                 150                 155                 160

Thr Asp His Ala Ile His Trp Val Lys Gln Asn Pro Glu Gln Gly Leu
                165                 170                 175

Glu Trp Ile Gly Tyr Phe Ser Pro Gly Asn Asp Asp Phe Lys Tyr Asn
            180                 185                 190

Glu Arg Phe Lys Gly Lys Ala Thr Leu Thr Ala Asp Lys Ser Ser Ser
        195                 200                 205

Thr Ala Tyr Val Gln Leu Asn Cys Leu Thr Ser Glu Asp Ser Ala Val
    210                 215                 220

Tyr Phe Cys Thr Arg Ser Leu Asn Met Ala Tyr Trp Gly Gln Gly Thr
225                 230                 235                 240

Ser Val Thr Val Ser Cys
```

-continued

245

(2) INFORMATION FOR SEQ ID NO: 3:

(i) SEQUENCE CHARACTERISTICS:
        (A) LENGTH: 782 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..771

(xi) SEQUENCE DESCRIPTION: SEQ ID NO: 3:

```
GAC GTC GTG ATG TCA CAG TCT CCA TCC TCC CTA CCT GTG TCA GTT GGC      48
Asp Val Val Met Ser Gln Ser Pro Ser Ser Leu Pro Val Ser Val Gly
        250                 255                 260

GAG AAG GTT ACT TTG AGC TGC AAG TCC AGT CAG AGC CTT TTA TAT AGT      96
Glu Lys Val Thr Leu Ser Cys Lys Ser Ser Gln Ser Leu Leu Tyr Ser
            265                 270                 275

GGT AAT CAA AAG AAC TAC TTG GCC TGG TAC CAG CAG AAA CCA GGG CAG     144
Gly Asn Gln Lys Asn Tyr Leu Ala Trp Tyr Gln Gln Lys Pro Gly Gln
280                 285                 290

TCT CCT AAA CTG CTG ATT TAC TGG GCA TCC GCT AGG GAA TCT GGG GTC     192
Ser Pro Lys Leu Leu Ile Tyr Trp Ala Ser Ala Arg Glu Ser Gly Val
295                 300                 305                 310

CCT GAT CGC TTC ACA GGC AGT GGA TCT GGG ACA GAT TTC ACT CTC TCC     240
Pro Asp Arg Phe Thr Gly Ser Gly Ser Gly Thr Asp Phe Thr Leu Ser
                315                 320                 325

ATC AGC AGT GTG AAG ACT GAA GAC CTG GCA GTT TAT TAC TGT CAG CAG     288
Ile Ser Ser Val Lys Thr Glu Asp Leu Ala Val Tyr Tyr Cys Gln Gln
            330                 335                 340

TAT TAT AGC TAT CCC CTC ACG TTC GGT GCT GGG ACC AAG CTT GTG CTG     336
Tyr Tyr Ser Tyr Pro Leu Thr Phe Gly Ala Gly Thr Lys Leu Val Leu
        345                 350                 355

AAA GGC TCT ACT TCC GGT AGC GGC AAA CCC GGG AGT GGT GAA GGT AGC     384
Lys Gly Ser Thr Ser Gly Ser Gly Lys Pro Gly Ser Gly Glu Gly Ser
360                 365                 370

ACT AAA GGT CAG GTT CAG CTG CAG CAG TCT GAC GCT GAG TTG GTG AAA     432
Thr Lys Gly Gln Val Gln Leu Gln Gln Ser Asp Ala Glu Leu Val Lys
375                 380                 385                 390

CCT GGG GCT TCA GTG AAG ATT TCC TGC AAG GCT TCT GGC TAC ACC TTC     480
Pro Gly Ala Ser Val Lys Ile Ser Cys Lys Ala Ser Gly Tyr Thr Phe
                395                 400                 405

ACT GAC CAT GCA ATT CAC TGG GTG AAA CAG AAC CCT GAA CAG GGC CTG     528
Thr Asp His Ala Ile His Trp Val Lys Gln Asn Pro Glu Gln Gly Leu
            410                 415                 420

GAA TGG ATT GGA TAT TTT TCT CCC GGA AAT GAT GAT TTT AAA TAC AAT     576
Glu Trp Ile Gly Tyr Phe Ser Pro Gly Asn Asp Asp Phe Lys Tyr Asn
        425                 430                 435

GAG AGG TTC AAG GGC AAG GCC ACA CTG ACT GCA GAC AAA TCC TCC AGC     624
Glu Arg Phe Lys Gly Lys Ala Thr Leu Thr Ala Asp Lys Ser Ser Ser
440                 445                 450

ACT GCC TAC GTG CAG CTC AAC AGC CTG ACA TCT GAG GAT TCT GCA GTG     672
Thr Ala Tyr Val Gln Leu Asn Ser Leu Thr Ser Glu Asp Ser Ala Val
455                 460                 465                 470

TAT TTC TGT ACA AGA TCC CTG AAT ATG GCC TAC TGG GGT CAA GGA ACC     720
Tyr Phe Cys Thr Arg Ser Leu Asn Met Ala Tyr Trp Gly Gln Gly Thr
                475                 480                 485
```

```
TCG GTC ACC GTC TCC AAA AAG AAG AAA AAA AAG AAA AAG GTC ACC GTC      768
Ser Val Thr Val Ser Lys Lys Lys Lys Lys Lys Lys Lys Val Thr Val
            490                 495                 500

TCC TAATAGGATC C                                                     782
Ser
```

(2) INFORMATION FOR SEQ ID NO: 4:

(i) SEQUENCE CHARACTERISTICS:
        (A) LENGTH: 257 amino acids
        (B) TYPE: amino acid
        (D) TOPOLOGY: linear (ii) MOLECULE TYPE: protein (xi) SEQUENCE DESCRIPTION: SEQ ID NO: 4:

```
Asp Val Val Met Ser Gln Ser Pro Ser Ser Leu Pro Val Ser Val Gly
 1               5                  10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
 65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
               100                 105                 110

Lys Gly Ser Thr Ser Gly Ser Gly Lys Pro Gly Ser Gly Glu Gly Ser
           115                 120                 125

Thr Lys Gly Gln Val Gln Leu Gln Gln Ser Asp Ala Glu Leu Val Lys
       130                 135                 140

Pro Gly Ala Ser Val Lys Ile Ser Cys Lys Ala Ser Gly Tyr Thr Phe
145                 150                 155                 160

Thr Asp His Ala Ile His Trp Val Lys Gln Asn Pro Glu Gln Gly Leu
               165                 170                 175

Glu Trp Ile Gly Tyr Phe Ser Pro Gly Asn Asp Asp Phe Lys Tyr Asn
           180                 185                 190

Glu Arg Phe Lys Gly Lys Ala Thr Leu Thr Ala Asp Lys Ser Ser Ser
       195                 200                 205

Thr Ala Tyr Val Gln Leu Asn Ser Leu Thr Ser Glu Asp Ser Ala Val
    210                 215                 220

Tyr Phe Cys Thr Arg Ser Leu Asn Met Ala Tyr Trp Gly Gln Gly Thr
225                 230                 235                 240

Ser Val Thr Val Ser Lys Lys Lys Lys Lys Lys Lys Val Thr Val
               245                 250                 255

Ser
```

(2) INFORMATION FOR SEQ ID NO: 5:

(i) SEQUENCE CHARACTERISTICS:
        (A) LENGTH: 723 base pairs
        (B) TYPE: nucleic acid
        (C) STRANDEDNESS: both
        (D) TOPOLOGY: both (ix) FEATURE:

(A) NAME/KEY: CDS
(B) LOCATION: 1..723

(xi) SEQUENCE DESCRIPTION: SEQ ID NO: 5:

| | | | | | | | | | | | | | | | | |
|---|---|---|---|---|---|---|---|---|---|---|---|---|---|---|---|---|
| GAC | GTC | GTG | ATG | TCA | CAG | TCT | CCA | TCC | TCC | CTA | CCT | GTG | TCA | GTT | GGC | 48 |
| Asp | Val | Val | Met | Ser | Gln | Ser | Pro | Ser | Ser | Leu | Pro | Val | Ser | Val | Gly | |
| 1 | | | | 5 | | | | | 10 | | | | | 15 | | |
| GAG | AAG | GTT | ACT | TTG | AGC | TGC | AAG | TCC | AGT | CAG | AGC | CTT | TTA | TAT | AGT | 96 |
| Glu | Lys | Val | Thr | Leu | Ser | Cys | Lys | Ser | Ser | Gln | Ser | Leu | Leu | Tyr | Ser | |
| | | | 20 | | | | | 25 | | | | | 30 | | | |
| GGT | AAT | CAA | AAG | AAC | TAC | TTG | GCC | TGG | TAC | CAG | CAG | AAA | CCA | GGG | CAG | 144 |
| Gly | Asn | Gln | Lys | Asn | Tyr | Leu | Ala | Trp | Tyr | Gln | Gln | Lys | Pro | Gly | Gln | |
| | | 35 | | | | | 40 | | | | | 45 | | | | |
| TCT | CCT | AAA | CTG | CTG | ATT | TAC | TGG | GCA | TCC | GCT | AGG | GAA | TCT | GGG | GTC | 192 |
| Ser | Pro | Lys | Leu | Leu | Ile | Tyr | Trp | Ala | Ser | Ala | Arg | Glu | Ser | Gly | Val | |
| 50 | | | | | 55 | | | | | 60 | | | | | | |
| CCT | GAT | CGC | TTC | ACA | GGC | AGT | GGA | TCT | GGG | ACA | GAT | TTC | ACT | CTC | TCC | 240 |
| Pro | Asp | Arg | Phe | Thr | Gly | Ser | Gly | Ser | Gly | Thr | Asp | Phe | Thr | Leu | Ser | |
| 65 | | | | 70 | | | | | 75 | | | | | 80 | | |
| ATC | AGC | AGT | GTG | AAG | ACT | GAA | GAC | CTG | GCA | GTT | TAT | TAC | TGT | CAG | CAG | 288 |
| Ile | Ser | Ser | Val | Lys | Thr | Glu | Asp | Leu | Ala | Val | Tyr | Tyr | Cys | Gln | Gln | |
| | | | | 85 | | | | | 90 | | | | | 95 | | |
| TAT | TAT | AGC | TAT | CCC | CTC | ACG | TTC | GGT | GCT | GGG | ACC | AAG | CTT | GTG | CTG | 336 |
| Tyr | Tyr | Ser | Tyr | Pro | Leu | Thr | Phe | Gly | Ala | Gly | Thr | Lys | Leu | Val | Leu | |
| | | | 100 | | | | | 105 | | | | | 110 | | | |
| AAA | GGC | TCT | ACT | TCC | GGT | AGC | GGC | AAA | TCC | TCT | GAA | GGC | AAA | GGT | CAG | 384 |
| Lys | Gly | Ser | Thr | Ser | Gly | Ser | Gly | Lys | Ser | Ser | Glu | Gly | Lys | Gly | Gln | |
| | | | 115 | | | | | 120 | | | | | 125 | | | |
| GTT | CAG | CTG | CAG | CAG | TCT | GAC | GCT | GAG | TTG | GTG | AAA | CCT | GGG | GCT | TCA | 432 |
| Val | Gln | Leu | Gln | Gln | Ser | Asp | Ala | Glu | Leu | Val | Lys | Pro | Gly | Ala | Ser | |
| | | 130 | | | | | 135 | | | | | 140 | | | | |
| GTG | AAG | ATT | TCC | TGC | AAG | GCT | TCT | GGC | TAC | ACC | TTC | ACT | GAC | CAT | GCA | 480 |
| Val | Lys | Ile | Ser | Cys | Lys | Ala | Ser | Gly | Tyr | Thr | Phe | Thr | Asp | His | Ala | |
| 145 | | | | | 150 | | | | | 155 | | | | | 160 | |
| ATT | CAC | TGG | GTG | AAA | CAG | AAC | CCT | GAA | CAG | GGC | CTG | GAA | TGG | ATT | GGA | 528 |
| Ile | His | Trp | Val | Lys | Gln | Asn | Pro | Glu | Gln | Gly | Leu | Glu | Trp | Ile | Gly | |
| | | | | 165 | | | | | 170 | | | | | 175 | | |
| TAT | TTT | TCT | CCC | GGA | AAT | GAT | GAT | TTT | AAA | TAC | AAT | GAG | AGG | TTC | AAG | 576 |
| Tyr | Phe | Ser | Pro | Gly | Asn | Asp | Asp | Phe | Lys | Tyr | Asn | Glu | Arg | Phe | Lys | |
| | | | 180 | | | | | 185 | | | | | 190 | | | |
| GGC | AAG | GCC | ACA | CTG | ACT | GCA | GAC | AAA | TCC | TCC | AGC | ACT | GCC | TAC | GTG | 624 |
| Gly | Lys | Ala | Thr | Leu | Thr | Ala | Asp | Lys | Ser | Ser | Ser | Thr | Ala | Tyr | Val | |
| | | | 195 | | | | | 200 | | | | | 205 | | | |
| CAG | CTC | AAC | AGC | CTG | ACA | TCT | GAG | GAT | TCT | GCA | GTG | TAT | TTC | TGT | ACA | 672 |
| Gln | Leu | Asn | Ser | Leu | Thr | Ser | Glu | Asp | Ser | Ala | Val | Tyr | Phe | Cys | Thr | |
| | | 210 | | | | | 215 | | | | | 220 | | | | |
| AGA | TCC | CTG | AAT | ATG | GCC | TAC | TGG | GGT | CAA | GGA | ACC | TCA | GTC | ACC | GTC | 720 |
| Arg | Ser | Leu | Asn | Met | Ala | Tyr | Trp | Gly | Gln | Gly | Thr | Ser | Val | Thr | Val | |
| 225 | | | | | 230 | | | | | 235 | | | | | 240 | |
| TCC | | | | | | | | | | | | | | | | 723 |
| Ser | | | | | | | | | | | | | | | | |

(2) INFORMATION FOR SEQ ID NO: 6:

(i) SEQUENCE CHARACTERISTICS:
        (A) LENGTH: 241 amino acids
        (B) TYPE: amino acid
        (D) TOPOLOGY: linear (ii) MOLECULE TYPE: protein (xi) SEQUENCE DESCRIPTION: SEQ ID NO: 6:

-continued

```
Asp Val Val Met Ser Gln Ser Pro Ser Ser Leu Pro Val Ser Val Gly
 1               5                  10                  15

Glu Lys Val Thr Leu Ser Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
            35                  40                  45

Ser Pro Lys Leu Leu Ile Tyr Trp Ala Ser Ala Arg Glu Ser Gly Val
        50                  55                  60

Pro Asp Arg Phe Thr Gly Ser Gly Ser Gly Thr Asp Phe Thr Leu Ser
 65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Gly Ser Thr Ser Gly Ser Gly Lys Ser Ser Glu Gly Lys Gly Gln
            115                 120                 125

Val Gln Leu Gln Gln Ser Asp Ala Glu Leu Val Lys Pro Gly Ala Ser
130                 135                 140

Val Lys Ile Ser Cys Lys Ala Ser Gly Tyr Thr Phe Thr Asp His Ala
145                 150                 155                 160

Ile His Trp Val Lys Gln Asn Pro Glu Gln Gly Leu Glu Trp Ile Gly
                165                 170                 175

Tyr Phe Ser Pro Gly Asn Asp Asp Phe Lys Tyr Asn Glu Arg Phe Lys
            180                 185                 190

Gly Lys Ala Thr Leu Thr Ala Asp Lys Ser Ser Ser Thr Ala Tyr Val
        195                 200                 205

Gln Leu Asn Ser Leu Thr Ser Glu Asp Ser Ala Val Tyr Phe Cys Thr
        210                 215                 220

Arg Ser Leu Asn Met Ala Tyr Trp Gly Gln Gly Thr Ser Val Thr Val
225                 230                 235                 240

Ser
```